US012558307B2

(12) United States Patent

Schoettle et al.

(10) Patent No.: US 12,558,307 B2

(45) Date of Patent: *Feb. 24, 2026

(54) INSULIN PREPARATIONS CONTAINING METHIONINE

(75) Inventors: Isabell Schoettle, Frankfurt am Main (DE); Annika Hagendorf, Frankfurt am Main (DE); Christiane Fuerst, Frankfurt am Main (DE); Gerrit Hauck, Frankfurt am Main (DE); Verena Siefke-Henzler, Frankfurt am Main (DE); Walter Kamm, Frankfurt am Main (DE); Julia Schnieders, Frankfurt am Main (DE)

(73) Assignee: SANOFI-AVENTIS, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,442

(22) PCT Filed: Jul. 2, 2010

(86) PCT No.: PCT/EP2010/059436

§ 371 (c)(1),
(2), (4) Date: Mar. 21, 2012

(87) PCT Pub. No.: WO2011/003822

PCT Pub. Date: Jan. 13, 2011

(65) Prior Publication Data

US 2012/0252724 A1     Oct. 4, 2012

Related U.S. Application Data

(60) Provisional application No. 61/264,356, filed on Nov. 25, 2009.

(30) Foreign Application Priority Data

Jul. 6, 2009   (DE) .......................... 102009031748.1
Mar. 27, 2010   (DE) .......................... 102010013134.2

(51) Int. Cl.
   *A61K 9/00*       (2006.01)
   *A61K 9/10*       (2006.01)
   *A61K 38/22*      (2006.01)
   *A61K 38/28*      (2006.01)
   *A61K 47/00*      (2006.01)
   *A61K 47/10*      (2017.01)
   *A61K 47/18*      (2017.01)
   *A61K 47/20*      (2006.01)
   *C07K 14/62*      (2006.01)

(52) U.S. Cl.
   CPC .............. *A61K 9/0019* (2013.01); *A61K 9/10* (2013.01); *A61K 38/2278* (2013.01); *A61K 38/28* (2013.01); *A61K 47/00* (2013.01); *A61K 47/183* (2013.01); *A61K 47/20* (2013.01); *C07K 14/62* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 3,758,683 A | | 9/1973 | Jackson |
| 3,868,358 A | | 2/1975 | Jackson |
| 4,153,689 A | | 5/1979 | Hirai et al. |
| 4,165,370 A | | 8/1979 | Coval |
| 4,258,134 A | * | 3/1981 | Yoshida et al. ............... 435/201 |
| 4,367,737 A | | 1/1983 | Kozam et al. |
| 4,608,364 A | | 8/1986 | Grau |
| 4,614,730 A | | 9/1986 | Hansen |
| 4,644,057 A | | 2/1987 | Bicker et al. |
| 4,689,042 A | | 8/1987 | Sarnoff et al. |
| 4,701,440 A | | 10/1987 | Grau |
| 4,731,405 A | | 3/1988 | Kirsch et al. |
| 4,783,441 A | | 11/1988 | Thurow |
| 4,839,341 A | | 6/1989 | Massey et al. |
| 4,885,164 A | | 12/1989 | Thurow |
| 4,959,351 A | | 9/1990 | Grau |
| 4,960,702 A | | 10/1990 | Rice et al. |
| 4,994,439 A | | 2/1991 | Longenecker et al. |
| 5,008,241 A | | 4/1991 | Markussen et al. |
| 5,034,415 A | | 7/1991 | Rubin |
| 5,070,186 A | | 12/1991 | Joergensen |
| 5,101,013 A | | 3/1992 | Dorschug et al. |
| 5,149,716 A | | 9/1992 | Vertesy et al. |
| 5,177,058 A | | 1/1993 | Dorschug |
| 5,227,293 A | | 7/1993 | Stengelin et al. |
| 5,253,785 A | | 10/1993 | Haber et al. |

(Continued)

FOREIGN PATENT DOCUMENTS

| | | |
|---|---|---|
| AU | 62066/86 | 3/1987 |
| AU | 1987-75916 | 1/1988 |

(Continued)

OTHER PUBLICATIONS

U.S. Appl. No. 13/509,542, filed Aug. 2012, Hagendorf et al.*

(Continued)

*Primary Examiner* — Thea D'Ambrosio

(74) *Attorney, Agent, or Firm* — McDonnell Boehnen Hulbert & Berghoff LLP

(57) ABSTRACT

The invention relates to an aqueous pharmaceutical formulation having insulin, an insulin analog, or an insulin derivative, and methionine; and to the production thereof, to the use thereof for treating diabetes mellitus, and to a medication for treating diabetes mellitus.

5 Claims, 6 Drawing Sheets

Figure 1:
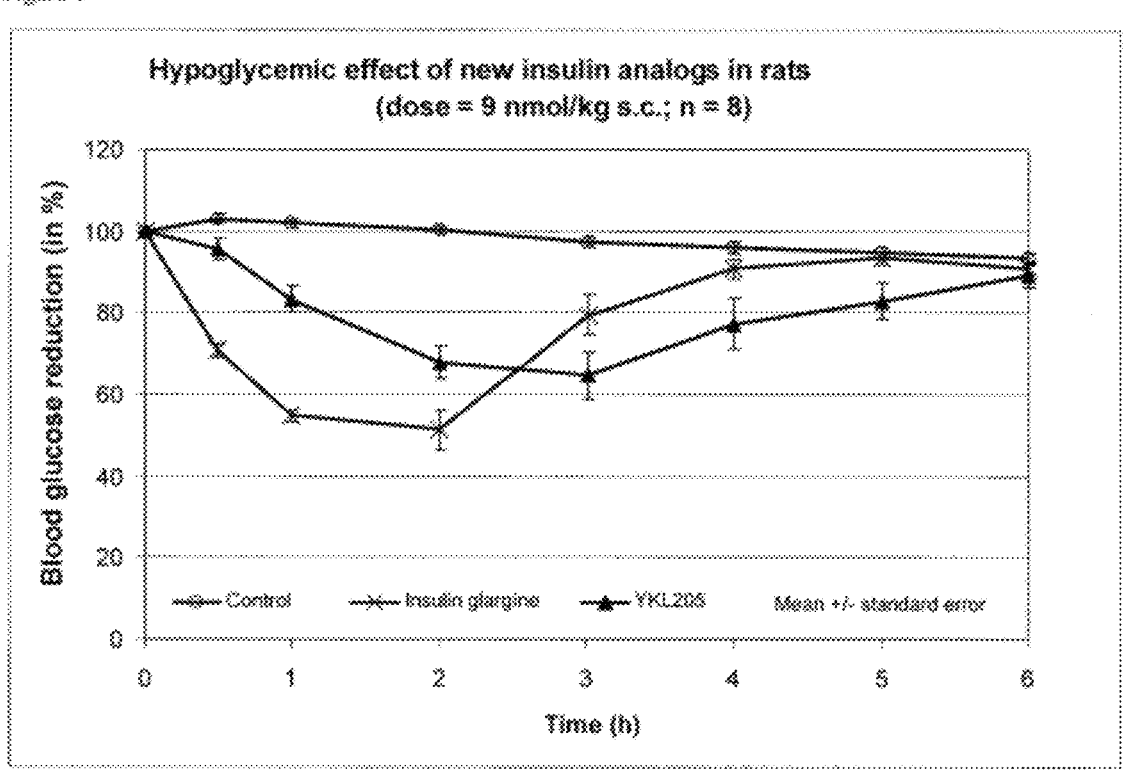

Specification includes a Sequence Listing.

(56) References Cited

U.S. PATENT DOCUMENTS

| | | | |
|---|---|---|---|
| 5,272,135 A | 12/1993 | Takruri | |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |
| 5,407,609 A | 4/1995 | Tice et al. | |
| 5,424,286 A | 6/1995 | Eng | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,478,323 A | 12/1995 | Westwood et al. | |
| 5,496,924 A | 3/1996 | Habermann et al. | |
| 5,506,203 A | 4/1996 | Backstrom et al. | |
| 5,509,905 A | 4/1996 | Michel | |
| 5,514,646 A | 5/1996 | Chance et al. | |
| 5,524,286 A | 6/1996 | Chiesa et al. | |
| 5,534,488 A | 7/1996 | Hoffman | |
| 5,545,618 A | 8/1996 | Buckley et al. | |
| 5,547,929 A | 8/1996 | Anderson, Jr. et al. | |
| 5,559,094 A | 9/1996 | Brems et al. | |
| 5,597,796 A | 1/1997 | Brange | |
| 5,614,219 A | 3/1997 | Wunderlich et al. | |
| 5,614,492 A | 3/1997 | Habener | |
| 5,631,224 A | 5/1997 | Efendic et al. | |
| 5,654,008 A | 8/1997 | Herbert et al. | |
| 5,656,722 A | 8/1997 | Dorschug | |
| 5,663,291 A | 9/1997 | Obermeier et al. | |
| 5,670,260 A | 9/1997 | Thorens | |
| 5,670,360 A | 9/1997 | Thorens | |
| 5,674,204 A | 10/1997 | Chanoch | |
| 5,693,608 A | 12/1997 | Bechgaard et al. | |
| 5,700,662 A | 12/1997 | Chance et al. | |
| 5,707,641 A | 1/1998 | Gertner et al. | |
| 5,783,556 A | 7/1998 | Clark et al. | |
| 5,824,638 A | 10/1998 | Burnside et al. | |
| 5,846,747 A | 12/1998 | Thorens et al. | |
| 5,846,937 A | 12/1998 | Drucker | |
| 5,866,538 A | 2/1999 | Norup et al. | |
| 5,879,584 A | 3/1999 | Bianchetti et al. | |
| 5,935,566 A | 8/1999 | Yuen et al. | |
| 5,948,751 A | 9/1999 | Kimer et al. | |
| 5,952,297 A | 9/1999 | De Felippis et al. | |
| 5,985,309 A | 11/1999 | Edwards et al. | |
| 6,006,753 A | 12/1999 | Efendic | |
| 6,034,054 A | 3/2000 | DeFelippis et al. | |
| 6,043,214 A | 3/2000 | Jensen et al. | |
| 6,051,551 A | 4/2000 | Hughes et al. | |
| 6,051,689 A | 4/2000 | Thorens | |
| 6,100,376 A | 8/2000 | Doerschug | |
| 6,110,703 A | 8/2000 | Egei-Mitani et al. | |
| 6,174,856 B1 * | 1/2001 | Langballe | A61K 9/0019 514/5.9 |
| 6,191,102 B1 | 2/2001 | DiMarchi et al. | |
| 6,211,144 B1 | 4/2001 | Havelund | |
| 6,227,819 B1 | 5/2001 | Gettel et al. | |
| 6,235,004 B1 | 5/2001 | Steenfeldt-Jensen et al. | |
| 6,248,095 B1 | 6/2001 | Giambattista et al. | |
| 6,248,363 B1 | 6/2001 | Patel et al. | |
| 6,265,335 B1 | 7/2001 | Oleske et al. | |
| 6,267,981 B1 | 7/2001 | Okamoto et al. | |
| 6,268,335 B1 | 7/2001 | Brader | |
| 6,268,343 B1 | 7/2001 | Knudsen et al. | |
| 6,271,241 B1 | 8/2001 | DeSimone et al. | |
| 6,284,725 B1 | 9/2001 | Coolidge et al. | |
| 6,309,663 B1 | 10/2001 | Patel et al. | |
| 6,310,038 B1 | 10/2001 | Havelund | |
| 6,329,336 B1 | 12/2001 | Briden et al. | |
| 6,335,316 B1 | 1/2002 | Hughes et al. | |
| 6,344,180 B1 | 2/2002 | Holst et al. | |
| 6,358,924 B1 | 3/2002 | Hoffmann | |
| 6,384,016 B1 | 5/2002 | Kaarsholm | |
| 6,388,053 B1 | 5/2002 | Galloway et al. | |
| 6,395,767 B2 | 5/2002 | Robl et al. | |
| 6,410,508 B1 | 6/2002 | Isales et al. | |
| 6,410,511 B2 | 6/2002 | L'Italien et al. | |
| 6,444,641 B1 | 9/2002 | Flora | |
| 6,468,959 B1 | 10/2002 | Wunderlich et al. | |
| 6,489,292 B1 | 12/2002 | Havelund et al. | |
| 6,528,486 B1 | 3/2003 | Larsen et al. | |
| 6,734,162 B2 | 5/2004 | Van Antwerp et al. | |
| 6,737,401 B2 | 5/2004 | Kim et al. | |
| 6,767,887 B1 | 7/2004 | Hoffmann et al. | |
| 6,818,738 B2 | 11/2004 | Havelund | |
| 6,852,694 B2 * | 2/2005 | Van Antwerp et al. | 514/6.3 |
| 6,875,589 B1 | 4/2005 | Dorschug et al. | |
| 6,902,744 B1 | 6/2005 | Kolterman et al. | |
| 6,908,610 B1 | 6/2005 | Sato | |
| 6,908,897 B2 | 6/2005 | Brandenburg et al. | |
| 6,960,561 B2 | 11/2005 | Boderke | |
| 7,022,674 B2 | 4/2006 | DeFelippis | |
| 7,115,563 B2 | 10/2006 | Younis | |
| 7,119,086 B2 | 10/2006 | Di Malta et al. | |
| 7,192,919 B2 | 3/2007 | Tzannis et al. | |
| 7,205,276 B2 | 4/2007 | Boderke | |
| 7,205,277 B2 * | 4/2007 | Boderke | 514/6.6 |
| 7,238,663 B2 | 7/2007 | DeFelippis et al. | |
| 7,405,196 B2 | 7/2008 | Rosskamp et al. | |
| 7,476,652 B2 | 1/2009 | Brunner-Schwarz et al. | |
| 7,544,656 B2 | 6/2009 | Sabetsky | |
| 7,544,657 B2 | 6/2009 | Ebbehoj et al. | |
| 7,713,930 B2 * | 5/2010 | Brunner-Schwarz et al. | 514/1.1 |
| 7,803,763 B2 | 9/2010 | Thurow et al. | |
| 7,807,242 B2 | 10/2010 | Soerensen et al. | |
| 7,918,833 B2 | 4/2011 | Veasey et al. | |
| 7,939,293 B2 | 5/2011 | Habermann et al. | |
| 7,977,310 B2 | 7/2011 | Rosskamp et al. | |
| 8,048,854 B2 * | 11/2011 | Habermann et al. | 514/6.3 |
| 8,084,420 B2 | 12/2011 | Steiner et al. | |
| 8,092,421 B2 | 1/2012 | Seiferlein et al. | |
| 8,092,422 B2 | 1/2012 | Seiferlein et al. | |
| 8,178,495 B2 | 5/2012 | Chilkoti | |
| 8,574,214 B2 | 11/2013 | Kuhn et al. | |
| 8,633,156 B2 | 1/2014 | Habermann et al. | |
| 9,345,750 B2 | 5/2016 | Becker et al. | |
| 10,029,011 B2 * | 7/2018 | Hagendorf | C07K 14/605 |
| 2001/0012829 A1 | 8/2001 | Anderson et al. | |
| 2001/0033868 A1 | 10/2001 | Rossling et al. | |
| 2001/0039260 A1 | 11/2001 | Havelund | |
| 2001/0047084 A1 | 11/2001 | Knudsen et al. | |
| 2002/0107265 A1 | 8/2002 | Chen et al. | |
| 2002/0132760 A1 | 9/2002 | Van Antwerp et al. | |
| 2002/0198140 A1 | 12/2002 | Havelund | |
| 2003/0004096 A1 | 1/2003 | Boderke | |
| 2003/0026872 A1 | 2/2003 | Dake et al. | |
| 2003/0212248 A1 | 11/2003 | Furman | |
| 2004/0022792 A1 | 2/2004 | Klinke | |
| 2004/0037893 A1 * | 2/2004 | Hansen | A61K 9/0019 424/682 |
| 2004/0048783 A1 | 3/2004 | Brunner-Schwarz et al. | |
| 2004/0097410 A1 | 5/2004 | Zheng et al. | |
| 2004/0106547 A1 | 6/2004 | Larsen et al. | |
| 2004/0235710 A1 | 11/2004 | DeFelippis et al. | |
| 2005/0014679 A1 | 1/2005 | Beals et al. | |
| 2005/0106147 A1 | 5/2005 | Jordan et al. | |
| 2005/0171009 A1 | 8/2005 | Brunner-Schwarz et al. | |
| 2006/0004049 A1 | 1/2006 | Yao et al. | |
| 2006/0014678 A1 | 1/2006 | Cowley et al. | |
| 2006/0019347 A1 | 1/2006 | Cho et al. | |
| 2006/0073213 A1 | 4/2006 | Hotamisligil et al. | |
| 2006/0093576 A1 | 5/2006 | Chen et al. | |
| 2006/0120969 A1 | 6/2006 | Nilsson et al. | |
| 2006/0194719 A1 | 8/2006 | Ebbehoj et al. | |
| 2006/0287221 A1 | 12/2006 | Knudsen et al. | |
| 2007/0111940 A1 | 5/2007 | Larsen et al. | |
| 2007/0128193 A1 | 6/2007 | O'Neil et al. | |
| 2007/0135338 A1 | 6/2007 | O'Neil et al. | |
| 2007/0155653 A1 | 7/2007 | Boderke | |
| 2007/0191271 A1 * | 8/2007 | Mayhew et al. | 514/12 |
| 2007/0237827 A1 | 10/2007 | Sung et al. | |
| 2008/0064856 A1 * | 3/2008 | Warne | A61K 9/0019 530/383 |
| 2008/0146490 A1 | 6/2008 | Joabsson et al. | |
| 2008/0248999 A1 * | 10/2008 | Steiner | 514/4 |

(56) References Cited

U.S. PATENT DOCUMENTS

| | | | |
|---|---|---|---|
| 2008/0260840 A1* | 10/2008 | Alessi et al. ................. | 424/489 |
| 2008/0267907 A1 | 10/2008 | Poulsen | |
| 2009/0082255 A1* | 3/2009 | Brunner-Schwarz et al. ... | 514/3 |
| 2009/0088369 A1 | 4/2009 | Steiness | |
| 2009/0099064 A1 | 4/2009 | Lougheed | |
| 2009/0142338 A1 | 6/2009 | Levetan | |
| 2009/0175840 A1 | 7/2009 | Kashyap et al. | |
| 2009/0176692 A1 | 7/2009 | Larsen et al. | |
| 2009/0186807 A1 | 7/2009 | Boderke et al. | |
| 2009/0186819 A1 | 7/2009 | Carrier et al. | |
| 2009/0208565 A1 | 8/2009 | Ebbehoj et al. | |
| 2009/0214468 A1* | 8/2009 | Lin ........................ | A61K 38/28 |
| | | | 424/85.2 |
| 2009/0214657 A1 | 8/2009 | Qazi | |
| 2009/0304665 A1* | 12/2009 | Frost et al. .................. | 424/94.5 |
| 2009/0312236 A1 | 12/2009 | Beals et al. | |
| 2009/0324701 A1 | 12/2009 | Williams | |
| 2010/0029558 A1 | 2/2010 | Bristow | |
| 2010/0055049 A1 | 3/2010 | Kuo et al. | |
| 2010/0057194 A1 | 3/2010 | Ryan | |
| 2010/0069292 A1 | 3/2010 | Pohl et al. | |
| 2010/0069293 A1 | 3/2010 | Bolotin et al. | |
| 2010/0227816 A1 | 9/2010 | Fiatt et al. | |
| 2010/0279931 A1 | 11/2010 | Garibay et al. | |
| 2010/0311112 A1 | 12/2010 | Rissom et al. | |
| 2011/0020294 A1 | 1/2011 | Hammerman | |
| 2011/0021423 A1 | 1/2011 | Olsen et al. | |
| 2011/0077197 A1* | 3/2011 | Habermann et al. .......... | 514/6.4 |
| 2011/0118178 A1 | 5/2011 | Silvestre et al. | |
| 2011/0118180 A1 | 5/2011 | Silverstre et al. | |
| 2011/0144008 A1 | 6/2011 | Larsen et al. | |
| 2011/0152185 A1 | 6/2011 | Plum et al. | |
| 2011/0173722 A1 | 7/2011 | Habermann et al. | |
| 2011/0230402 A1 | 9/2011 | Johansen et al. | |
| 2011/0236925 A1 | 9/2011 | Hazra et al. | |
| 2011/0245165 A1 | 10/2011 | Larsen et al. | |
| 2011/0281790 A1 | 11/2011 | Pohl et al. | |
| 2011/0301081 A1 | 12/2011 | Becker et al. | |
| 2012/0021978 A1* | 1/2012 | Werner et al. ................ | 514/6.2 |
| 2012/0121611 A1 | 5/2012 | Lodie et al. | |
| 2012/0122774 A1 | 5/2012 | Becker et al. | |
| 2012/0183616 A1 | 7/2012 | Sprogoe et al. | |
| 2012/0184489 A1 | 7/2012 | Rau et al. | |
| 2012/0232002 A1* | 9/2012 | Schoettle et al. ............. | 514/6.2 |
| 2012/0241356 A1 | 9/2012 | Pfenninger et al. | |
| 2012/0252724 A1 | 10/2012 | Schoettle et al. | |
| 2012/0277147 A1 | 11/2012 | Boka et al. | |
| 2012/0283179 A1* | 11/2012 | Brunner-Schwarz et al. ............. | |
| | | | 514/5.3 |
| 2012/0295846 A1* | 11/2012 | Hagendorf et al. ........... | 514/6.5 |
| 2012/0316108 A1 | 12/2012 | Chen et al. | |
| 2013/0005649 A1 | 1/2013 | Niemoeller et al. | |
| 2013/0011378 A1 | 1/2013 | Yang et al. | |
| 2013/0012422 A1 | 1/2013 | Rosskamp et al. | |
| 2013/0023467 A1 | 1/2013 | Silvestre et al. | |
| 2013/0040878 A1 | 2/2013 | Silvestre et al. | |
| 2013/0065828 A1 | 3/2013 | Ruus et al. | |
| 2013/0079279 A1 | 3/2013 | Becker et al. | |
| 2013/0085102 A1 | 4/2013 | Silvestre et al. | |
| 2013/0096059 A1 | 4/2013 | Stechl et al. | |
| 2013/0096060 A1 | 4/2013 | Stechl et al. | |
| 2013/0203666 A1 | 8/2013 | Niemoeller et al. | |
| 2013/0284912 A1 | 10/2013 | Vogel et al. | |
| 2013/0296236 A1 | 11/2013 | Silvestre et al. | |
| 2014/0024582 A1 | 1/2014 | Yang et al. | |
| 2014/0142034 A1 | 5/2014 | Soula et al. | |
| 2014/0148384 A1 | 5/2014 | Boka et al. | |
| 2014/0206611 A1* | 7/2014 | Becker et al. ................. | 514/6.5 |
| 2014/0248365 A1 | 9/2014 | Rademacher et al. | |
| 2015/0119323 A1 | 4/2015 | Loos et al. | |
| 2015/0190475 A1 | 7/2015 | Bley et al. | |
| 2018/0036411 A1* | 2/2018 | Loos ........................ | A61K 38/28 |
| 2020/0188516 A1* | 6/2020 | Hagendorf ................ | A61P 3/04 |
| 2021/0038514 A1* | 2/2021 | Brunner-Schwarz ..... | A61P 3/10 |
| 2022/0133890 A1* | 5/2022 | Hagendorf ............ | A61K 47/20 |
| | | | 514/6.5 |
| 2023/0028647 A1* | 1/2023 | Brunner-Schwarz ........................ | |
| | | | A61K 38/26 |

FOREIGN PATENT DOCUMENTS

| | | | |
|---|---|---|---|
| AU | 2000-72263 | | 2/2001 |
| CA | 1173388 | | 8/1984 |
| CA | 1258427 | | 8/1989 |
| CA | 1336329 | | 7/1995 |
| CA | 1341203 | | 3/2001 |
| CN | 1276731 | | 12/2000 |
| CN | 1630709 | | 6/2005 |
| CN | 1662252 | | 8/2005 |
| CN | 101366692 | | 2/2009 |
| CN | 101444618 | | 6/2009 |
| CN | 101454019 | | 6/2009 |
| CN | 101670096 | | 3/2010 |
| DE | 2 219 635 | | 11/1972 |
| DE | 3 240 177 | | 5/1983 |
| DE | 19637230 | | 3/1998 |
| DE | 10 2008 003 566 | | 7/2009 |
| DE | 10 2008 003 568 | | 7/2009 |
| DE | 102008053048 | | 4/2010 |
| EA | 006019 | | 8/2005 |
| EP | 0018609 | | 11/1980 |
| EP | 0046979 | | 3/1982 |
| EP | 0 124 826 | | 11/1984 |
| EP | 0132769 | | 2/1985 |
| EP | 0140084 | | 5/1985 |
| EP | 0166529 | A1 | 1/1986 |
| EP | 0194864 | | 3/1986 |
| EP | 0 180 920 | | 5/1986 |
| EP | 0200383 | | 12/1986 |
| EP | 0211299 | | 2/1987 |
| EP | 0 214 823 | | 3/1987 |
| EP | 0214826 | A2 | 3/1987 |
| EP | 0214826 | B1 | 3/1987 |
| EP | 0224885 | A1 | 6/1987 |
| EP | 0227938 | | 7/1987 |
| EP | 0229956 | | 7/1987 |
| EP | 0229998 | | 7/1987 |
| EP | 0254516 | | 1/1988 |
| EP | 0305760 | | 3/1989 |
| EP | 0 419 504 | | 11/1989 |
| EP | 0 368 187 | | 5/1990 |
| EP | 0 375 437 | | 6/1990 |
| EP | 0375437 | B1 | 6/1990 |
| EP | 0383472 | | 8/1990 |
| EP | 0 294 851 | | 10/1990 |
| EP | 0600372 | | 6/1994 |
| EP | 0668282 | | 8/1995 |
| EP | 0668292 | | 8/1995 |
| EP | 0 678 522 | | 10/1995 |
| EP | 0678522 | A1 | 10/1995 |
| EP | 0 376 156 | | 3/1996 |
| EP | 0837072 | | 4/1998 |
| EP | 0845265 | | 6/1998 |
| EP | 0 885 961 | | 12/1998 |
| EP | 1076066 | | 2/2001 |
| EP | 1172114 | | 1/2002 |
| EP | 1222207 | | 7/2002 |
| EP | 1 364 032 | | 11/2003 |
| EP | 1 523 993 | | 4/2005 |
| EP | 1 197 221 | | 5/2006 |
| EP | 1 906 991 | | 4/2008 |
| EP | 2 187 950 | | 5/2010 |
| EP | 2389945 | | 11/2011 |
| EP | 2329848 | | 10/2012 |
| EP | 2387989 | | 7/2014 |
| FR | 2456522 | | 12/1980 |
| GB | 1527605 | | 10/1978 |
| GB | 1554157 | | 10/1979 |
| JP | 61212598 | | 9/1986 |
| JP | 6399096 | | 9/1988 |
| JP | 2218696 | | 8/1990 |
| JP | 2-264798 | | 10/1990 |

(56) References Cited

FOREIGN PATENT DOCUMENTS

| | | |
|---|---|---|
| JP | 3504240 | 9/1991 |
| JP | 6506444 | 7/1994 |
| JP | 2001521004 | 11/2001 |
| JP | 2002516880 A | 6/2002 |
| JP | 2005-508895 | 4/2005 |
| JP | 2005-532365 | 10/2005 |
| JP | 2006137678 | 1/2006 |
| JP | 2006-515267 | 5/2006 |
| JP | 2007204498 A1 | 8/2007 |
| JP | 200991363 A | 4/2009 |
| JP | 2012-505852 | 3/2012 |
| JP | 2012-255040 | 12/2012 |
| RU | 2008116057 | 10/2009 |
| TW | 157005 | 5/1991 |
| TW | 562806 | 11/2003 |
| WO | WO 83/00288 | 2/1983 |
| WO | 88/06599 | 9/1988 |
| WO | WO 89/10937 | 11/1989 |
| WO | 90/07522 | 7/1990 |
| WO | 9011299 | 10/1990 |
| WO | 9103550 | 3/1991 |
| WO | 91/16929 | 11/1991 |
| WO | WO92/00321 | 1/1992 |
| WO | 9212999 | 8/1992 |
| WO | 1993/018786 | 9/1993 |
| WO | 94/14461 | 7/1994 |
| WO | 1995/024183 | 9/1995 |
| WO | 96/04307 | 2/1996 |
| WO | 96/07399 | 3/1996 |
| WO | 96/11706 | 4/1996 |
| WO | WO 96/32414 | 10/1996 |
| WO | 9634882 | 11/1996 |
| WO | 96/41606 | 12/1996 |
| WO | 9701331 | 1/1997 |
| WO | 9748413 | 12/1997 |
| WO | 1998/005351 | 2/1998 |
| WO | 1998/008531 | 3/1998 |
| WO | 1998/008873 | 3/1998 |
| WO | 9808871 | 3/1998 |
| WO | 1998/019698 | 5/1998 |
| WO | 1998/030231 | 7/1998 |
| WO | 1998/035033 | 8/1998 |
| WO | 1998/039022 | 9/1998 |
| WO | 98/42749 | 10/1998 |
| WO | 98/56406 | 12/1998 |
| WO | WO 98/56418 | 12/1998 |
| WO | 1999/007404 | 2/1999 |
| WO | 99/24071 | 5/1999 |
| WO | 1999/021573 | 5/1999 |
| WO | 1999/025727 | 5/1999 |
| WO | 1999/025728 | 5/1999 |
| WO | 1999/040788 | 8/1999 |
| WO | 1999/043708 | 9/1999 |
| WO | 1999/046283 | 9/1999 |
| WO | 1999062558 A1 | 12/1999 |
| WO | WO 99/62558 | 12/1999 |
| WO | 00/23098 | 4/2000 |
| WO | 00/23099 | 4/2000 |
| WO | 00/29013 | 5/2000 |
| WO | WO 00/051629 | 9/2000 |
| WO | 2000/066629 | 11/2000 |
| WO | 2000/072582 | 11/2000 |
| WO | 0074736 A1 | 12/2000 |
| WO | WO 01/02039 | 1/2001 |
| WO | WO 0104156 A1 * | 1/2001 | .......... C07K 14/575 |
| WO | 01/12155 | 2/2001 |
| WO | 01/21154 | 3/2001 |
| WO | 01/00223 | 4/2001 |
| WO | 01/28555 | 4/2001 |
| WO | WO 01/24814 | 4/2001 |
| WO | WO 01/25278 A1 | 4/2001 |
| WO | 01/37808 | 5/2001 |
| WO | 01/43762 | 6/2001 |
| WO | 01/52937 | 7/2001 |
| WO | 2001/051071 | 7/2001 |
| WO | 0193837 | 12/2001 |
| WO | 02000243 | 1/2002 |
| WO | 2002/024214 | 3/2002 |
| WO | 02064115 | 8/2002 |
| WO | 02065985 | 8/2002 |
| WO | 02066628 | 8/2002 |
| WO | 02068660 | 9/2002 |
| WO | 02070722 | 9/2002 |
| WO | 02/076495 | 10/2002 |
| WO | WO 02/079250 A1 | 10/2002 |
| WO | WO 02/092165 | 11/2002 |
| WO | 2003/002021 | 1/2003 |
| WO | 2003/020201 | 3/2003 |
| WO | WO 03/033671 | 4/2003 |
| WO | 03035028 | 5/2003 |
| WO | 03035051 | 5/2003 |
| WO | 03044210 | 5/2003 |
| WO | WO 03/053339 A2 | 7/2003 |
| WO | 03066084 | 8/2003 |
| WO | 2003/105888 | 12/2003 |
| WO | 03101395 A2 | 12/2003 |
| WO | 2003101395 A1 | 12/2003 |
| WO | 2004005342 | 1/2004 |
| WO | WO 2004/0035623 A2 | 4/2004 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | 2004096854 | 11/2004 |
| WO | 2005/021022 | 3/2005 |
| WO | 2005/028516 | 3/2005 |
| WO | 2005/046716 | 5/2005 |
| WO | 2005/048950 | 6/2005 |
| WO | WO 2005/061222 | 7/2005 |
| WO | 2005/112949 | 12/2005 |
| WO | 2005117948 | 12/2005 |
| WO | WO 2006/000567 | 1/2006 |
| WO | 2006015879 | 2/2006 |
| WO | 2006/029634 | 3/2006 |
| WO | 2006/051103 | 5/2006 |
| WO | 2006/051110 | 5/2006 |
| WO | WO 2006/051163 | 5/2006 |
| WO | WO 2006/058620 | 6/2006 |
| WO | 2006/083952 | 8/2006 |
| WO | 2006/110551 | 10/2006 |
| WO | WO 2006/131730 | 12/2006 |
| WO | 2007031187 | 3/2007 |
| WO | 2007/044867 | 4/2007 |
| WO | 2007036299 | 4/2007 |
| WO | 2007037607 A1 | 4/2007 |
| WO | WO 2007/037607 | 5/2007 |
| WO | WO 2007/050656 | 5/2007 |
| WO | 2007/082381 | 7/2007 |
| WO | 2007081821 | 7/2007 |
| WO | WO 2007/081824 A2 | 7/2007 |
| WO | WO 2007/095288 A2 | 8/2007 |
| WO | 2007/104786 | 9/2007 |
| WO | 2007109221 A2 | 9/2007 |
| WO | 2007/113205 | 10/2007 |
| WO | 2007/120899 | 10/2007 |
| WO | 2008/013938 | 1/2008 |
| WO | WO 2008/006496 A1 | 1/2008 |
| WO | WO 2008/016729 | 2/2008 |
| WO | WO 2008/023050 | 2/2008 |
| WO | 2008/034881 | 3/2008 |
| WO | 2008/124522 | 10/2008 |
| WO | WO 2008/124522 A2 | 10/2008 |
| WO | WO 2008/133908 A2 | 11/2008 |
| WO | 2008145323 | 12/2008 |
| WO | WO 2009024015 | 2/2009 |
| WO | 2009004627 A3 | 4/2009 |
| WO | WO 2009/039963 | 4/2009 |
| WO | WO 2009/048959 A1 | 4/2009 |
| WO | 2009/063072 | 5/2009 |
| WO | 2009056569 A1 | 5/2009 |
| WO | WO 2009/087081 A2 | 7/2009 |
| WO | WO 2009/087082 | 7/2009 |
| WO | WO 2009/089181 | 7/2009 |
| WO | 2009/102467 | 8/2009 |

(56)                References Cited

FOREIGN PATENT DOCUMENTS

| WO | 2009098318 | 8/2009 |
| WO | WO 2009/134380 A2 | 11/2009 |
| WO | WO 2009/143014 | 11/2009 |
| WO | 2010/030670 | 3/2010 |
| WO | 2010/044867 | 4/2010 |
| WO | WO 2010/043566 | 4/2010 |
| WO | 2010/092163 | 8/2010 |
| WO | WO 2011/003822 | 1/2011 |
| WO | WO 2011/003823 | 1/2011 |
| WO | 2011/012719 | 3/2011 |
| WO | 2011/029892 | 3/2011 |
| WO | 2011/058082 | 5/2011 |
| WO | 2011/058083 | 5/2011 |
| WO | WO 2011/085393 | 7/2011 |
| WO | 2011/103575 | 8/2011 |
| WO | 2011/122921 | 10/2011 |
| WO | 2011/128374 | 10/2011 |
| WO | 2011/144674 | 11/2011 |
| WO | 2011144673 | 11/2011 |
| WO | 2011/147980 | 12/2011 |
| WO | WO 2011/157402 | 12/2011 |
| WO | WO 2011/160066 | 12/2011 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | 2012/104342 | 8/2012 |
| WO | 2012/125569 | 9/2012 |
| WO | WO 2012/174478 | 12/2012 |
| WO | WO 2015/059302 | 4/2015 |

OTHER PUBLICATIONS

U.S. Appl. No. 13/509,507, filed Jul. 2012, Brenner-Schwarz et al.*
Campbell, et al., "Insulin Glargine," Clin. Therapeutics 23:1938-1957 (2001).*
Davis, How to Convert mg to mmol/L, available online at http://www.ehow.com/how_8498850_convert-mg-mmoll.html (accessed on Aug. 3, 2015).*
Chi Ey, available online at https://www.aaps.org/uploadedFiles/Content/Sections_and_Groups/Sections/Formulation_Design_And_Development_Section/FDDTechCornerMay2012.pdf, 9 pages (2012).*
Patel et al., "Stability Considerations for Biopharmaceuticals: Overview of Protein and Peptide Degradation Pathways" available online at: http://www.bioprocessintl.com/manufacturing/formulation/biopharmaceutical-product-stability-considerations-part-1/, 23 pages (2011).*
Anton Paar, "Shedding Light on Insulin Aggregation with the Litesizer™ 500," available online at www.anton-paar.com, 4 pages (2014) (Year: 2014).*
Iannuzzi et al, Intl. J. Molec. Sci. 18:14 pages (2017) (Year: 2017).*
Berhanu et al., J. Mol. Model 18:1129-1142 (2012) (Year: 2012).*
U.S. Appl. No. 17/366,332, filed Jul. 2021, Hagendorf et al.*
Lang et al., Polymers 12:25 pages (2020) (Year: 2020).*
"Liquid", The Britannica Dictionary, available online at www.britannica.com/dictionary/liquid, 2 pages (accessed on Nov. 17, 2023) (Year: 2023).*
Britannica, available online at: www.britannica.com/technology/pharmaceutical-industry/Safety-testing-in-animals#ref624890, 21 pages (accessed on Nov. 17, 2023) (Year: 2023).*
U.S. Appl. No. 18/647,078, Aug. 7, 2024, Hagendorf et al.*
Sanofi Aventis, available online at www.sanofi.com/assets/dotcom/content-app/clinical-studies/pharma/Letter-N/TDU10987_summary.pdf, 5 pages (2007) (Year: 2007).*
Brange, Jens et al. "Toward Understanding Insulin Fibrillation," Journal of Pharmaceutical Sciences (1997), vol. 86, No. 5, pp. 517-525.
Wan, Zhuli et al., "Enhancing the Activity of Insulin at the Receptor Interface: Crystal Structure and Photo-Cross-Linking of A8 Analogues," Biochemistry (2004), vol. 43, pp. 16119-16133.

The New England Journal of Medicine (1993), vol. 329, No. 14, pp. 977-986.
Brange J., "Design of Insulin Analogues for Meal-Related Therapy", J. Diabetes Complications 7(2):106-112 (Apr.-Jun. 1993), Abstract only.
Tessari P. et al., "Insulin in Methionine and Homocysteine Kinetics in Healthy Humans: Plasma Vs. Intracellular Models", Am J. Physiol Endocrinol Metab 288(6):E1270-E1276 (Jun. 2005).
Yu Z.P. et al., "Effect of Zinc Sulphate and Zinc Methionine on Growth, Plasma Growth Hormone Concentration, Growth Hormone Receptor and Insulin-Like Growth Factor-I Gene Expression in Mice", Clin Exp Pharmacol Physiol 32(4):273-278 (Apr. 2005), Abstract only.
English-language translation of Official Action dated Feb. 24, 2014 received from the Colombian Patent Office from related Application No. 12 001866.
Knudsen L.B. et al., "Potent Derivatives of Glucagon-Like Peptide-1 With Pharmacokinetic Properties Suitable for Once Daily Administration", J. Med. Chem. 43:1664-1669 (2000).
Weiss M.A. et al., "Activities of Monomeric Insulin Analogs at Position A8 Are Uncorrelated With Their Thermodynamic Stabilities", The Journal of Biological Chemistry 276(43):40018-40024 (Oct. 26, 2001).
Machine translation of WO 2008/006496, 13 pages, obtained at Espacenet.com on Nov. 7, 2013.
English-language translations of Bolivian Oppositions dated Oct. 25, 2012 filed by the Chamber of the Pharmaceutical Industry Boliviana against Application No. SP-0204-2010.
International Preliminary Report on Patentability dated Jan. 10, 2012 issued in Application No. PCT/EP2010/059438.
New Zealand Examination Report dated Nov. 4, 2013 received from related Application No. 597757.
U.S. Office Action dated Nov. 21, 2013 received from related U.S. Appl. No. 13/382,772.
U.S. Office Action dated Apr. 10, 2013 received from related U.S. Appl. No. 13/382,772.
Chilean Patent Application No. 026-2012, Opposition Proceeding, p. 1-7 (Jan. 23, 2014).
Japanese Application No. 2012-518919, Notification of Reasons for Refusal, p. 1-3 (Jul. 29, 2014).
Colombian Application No. 12 001866, Official Action No. 6907, p. 1-4 (Sep. 9, 2014).
Taiwan Patent Application No. 99121771, Office Action No. 10320876680, p. 1-8 (Jun. 26, 2014).
Beintema and Campagne, "Molecular Evolution of Rodent Insulins," Mol. Bioi. Evol. 4(1): 10-18, 1987.
European Search Report for European Patent Application No. 98110889.7 dated Oct. 14, 1998 (mailed Oct. 23, 1998) p. 1-4.
D.L. Bakaysa et al., "Physiochemical basis for the rapid time-action of LysB28 ProB28"—Insulin: Dissociation or a protein-ligand complex, Protein Science 5:2521-31 (1996).
Fransson et al., "Oxidation of Human Insulin-Like Growth Factor I in Formulation Studies: Kinetics of Methionine Oxidation in Aqueous Solution and in Solid State" Pharmaceutical Research, 1996, vol. 13, No. 8, pp. 1252-1257 (Aug. 1996).
Levine, R. L. et al., "Oxidation of Methionine in Proteins: Roles in Antioxidant Defense and Cellular Regulation" IUBMB Life, 2000, 50, pp. 301-307 (Oct. 2000).
Whittingham, J. L., et. al., Insulin at PH2: Structural Analysis of the Conditions Promoting Insulin Fibre Formation, J. Mol. Bioi., (2002), vol. 318, pp. 479-490.
American Diabetes Association, "Report of the Expert Committee on the Diagnosis and Classification of Diabetes Mellitus," Diabetes Care 21 (Supplement 1):S5-19 (1998).
Arnolds et al., "Insulin Glargine (GLAR) plus Metformin (MET): An Efficacious and Safe Regimen That Can Be Combined with Exenatide (EXE) or Sitagliptin (SIT A)," Diabetes, American Diabetes Association, vol. 58 (2009).
Arnolds & Rave, "Basal insulin glargine vs prandial insulin lispro in type 2 diabetes," Lancet 378(9636):370-71 (2008).
Byrne et al., "Inhibitory Effects of Hyperglycemia on Fed Jejunal Motility: Potential Role of Hyperinsulinaemia," Euro. J. Clin. Invest. 28(1):72-78 (1998).

(56)         References Cited

OTHER PUBLICATIONS

Chatterjee et al., "Insulin glargine and its place in the treatment of Types 1 and 2 diabetes mellitus," Expert Opin Pharmacother. 7(10):1357-71 (2006).
Chen et al., "Tissue-specific Expression of Unique mRNAs That Encode Proglucagon-derived Peptides or Exendin 4 in the Lizard," J. Biol. Chem. 272(7):4108-15 (1997).
Christensen et al., "Lixisenatide, a Novel GLP-1 Receptor Agonist for the Treatment of Type 2 Diabetes Millitus," IDrugs 12(8):503-13 (2009).
Cochran et al., "The Use of U-500 in Patients with Extreme Insulin Resistance," Diabetes Care 28(5):1240-4 (2005).
Colino et al., "Therapy with insulin glargine (Lantus) in toddlers, children and adolescents with type 1 diabetes," Diabetes Res Clin Pract. 70(1):1-7 (2005).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
De Le Pena et al., "Pharmacokinetics and Pharmadynamics of High-Dose Human Regular U-500 Insulin Versus Human Regular U-100 Insulin in Healthy Obese Subjects", Diabetes Care 34(12):2496-501 (2011).
Drucker, "The Biology of Incretin Hormones," Cell Metab. 3(3):153-65 (2006).
Drucker, "Glucagon-Like Peptides," Diabetes 47(2):159-69 (1998).
Drucker, "Mini review: The Glucagon-Like Peptides," Endocrinology 142(2):521-27 (2001).
DrugBank, "Insulin glargine," available online at http://www.drugbank.ca/drugs/DB00047, 16 pages (accessed online Sep. 25, 2014).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
Fieller, "Some Problems with Interval Estimation," Journal of the Royal Statistical Society, Series B (Methodological) 16(2):175-85 (1954).
Garg et al., "U-500 insulin: why, when and how to use in clinical practice," Diabetes Metab Res Rev 23:265-8 (2007).
Goke et al., "Distribution of GLP-1 Binding Sites in the Rat Brain: Evidence that Exendin-4 is a Ligand of Brain GLP-1 Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Gough et al., "Assessment of Dose Proportionality: Report from the Statisticians in the Pharmaceutical Industry/ Pharmacokinetics UK Joint Working Party," Drug Information Journal 29:1039-48 (1995).
Greig et al., "Once Daily Injection of Exendin-4 to Diabetic Mice Achieves Long-Term Beneficial Effects on Blood Glucose Concentrations." Diabetologia 42(1):45-50 (1999).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).

HOE 901/2004 Study Investigators Group, "Safety and efficacy of insulin glargine (HOE 901) versus NPH insulin in combination with oral treatment in Type 2 diabetic patients," Diabetic Medicine 20 545-51 (2003).
Holst, "Glucagon-like Peptide-1, a Gastrointestinal Hormone with a Pharmaceutical Potential," Current Medicinal Chemistry 6:1005-17 (1999).
Johnson & Shimshi, "When is a unit of insulin not a unit of insulin? Detemir dosing in type 2 diabetes," http://professional.diabetes.org/ContenUPosters/2008/p8-LB.pdf (2008).
Jorgensen et al., "Five fold increase of insulin concentration delays the absorption of subcutaneously injected human insulin suspension in pigs", Diabetes Res Clin Pract. 50(3):161-7 (2000).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Knee et al., "A Novel Use of U-500 Iunsulin for Continuous Subcutaneous Insulin Infusion in Patients With Insulin Resistance: A Case Series", Endocr Pract. 9(3):181-6 (2003).
Lando, "The New Designer Insulins," Clinical Diabetes 18(4), http://journal.diabetes.org/clinical diabetes/v18N42000/pg154.htm (2000).
Larsen et al., "Sequence-Assisted Peptide Synthesis (SAPS)," J. Pept. Res. 52(6):470-76 (1998).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Merrifield, "Solid Phase Synthesis." Science 232(4748):341-47 (1986).
Nathan et al., "Insulinotropic Action of Glucagon like Peptide-1-(7-37) in Diabetic and Nondiabetic Subjects," Diabetes Care 15(2):270-76 (1992).
Nauck et al., "Effects of Subcutaneous Glucagon-Like Peptide 1 (GLP-1 [7-36 Amide]) in Patients with NIDDM," Diabetologia 39(12):1546-53 (1996).
Nauck et al., "Glucagon-like peptide 1 (GLP-1) as a new therapeutic approach for type 2-diabetes," Exp Clin Endocrinol. Diabetes 105(4):187-95 (1997).
Nauck et al., "Glucagon-Like Peptide 1 and its Potential in the Treatment of Non-Insulin-Dependent Diaetes Mellitus," Horm. Metab. Res. 29(9):411-16 (1997).
Needleman et al., "A General Method Applicable to the Search for Similarities in the Amino Acid Sequence of Two Proteins," J. Mol. Biol. 48:443-453 (1970).
"NDA 21-081 Draft Package Insert," Sponsor revision #5, Date of submission: Apr. 20, 2000 http://www.drugbank.ca/system/fda_labels/DB00047.pdf (14 pages).
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Noble, et al., "Insulin Lispro: A Fast-Acting Insulin Analog," Am Fam Physician, 57(2):279-86 (1998).
Organization for Economic Co-Ooperation and Development, "OECD Principles of Good Laboratory Practice and Compliance Monitoring," ENV/MC/CHEM (98)17 (1998) (40 pages).
Orskov, "Glucagon-like Peptide-1, a New Hormone of the Enteroinsular Axis," Diabetologia 35(8):701-711 (1992).
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Pohl & Wank, "Molecular Cloning of the Heloderman and Exendin-4 cDNAs in the Lizard," J. Biol. Chem. 273(16):9778-84 (1998).
Raufman, "Bioactive peptides from lizard venoms," Regul Pept 61(1):1-18 (1996).
Ritzel et al., "A Synthetic Glucagon-Like Peptide-1 Analog with Improved Plasma Stability," J. Endocrine. 159(1):93-102 (1998).
Sampson et al., "Second Symposium on the definition and management of anaphylaxis: Summary report—Second National Institute of Allergy and Infectious Disease/Food Allergy and Anaphylaxis network symposium," J Allergy Clin Immunol 117(2:391-7 (2006).

(56)                 References Cited

OTHER PUBLICATIONS

Secnik Boye et al., "Patient-reported outcomes in a trial of exenatide and insulin glargine for the treatment of type 2 diabetes," Health and Quality of Life Outcomes 4:80 (2006).
"Suspension," Taber's Cyclopedic Medical Dictionary, 19th Edition, p. 2097 (F.A. Davis Co., Philadelphia 2001).
"Suspension," Stedman's Medical Dictionary, 20th Edition, p. 1450 (Williams & Wilkins Co., Baltimore 1961).
Tews et al., "Enhanced Protection against Cytokine- and Fatty Acid-induced Apoptosis in Pancreatic Beta Cells by Combined Treatment with Glucagon-like Peptide-1 Receptor Agonists and Insulin Analogues," Hormone and Metabolic Research 40(3):172-80 (2008).
Uttenthal et al., "Molecular forms of flucagon-like peptide-1 in human pancreas and glucagonomas," J. Clin. Endocrinol. Metabol. 61(3):472-79 (1985).
Wafa et al., "Use of U-500 Regular Insulin in Type 2 Diabetes", Diabetes Care 29(9):2175-6 (2006).
Werner et al., "Insulin Glargine U-100 Has a Favourable Time-Action Profile Compared to U-40 or NPH Insulin in Healthy, Normoglycaemic Dogs," Poster and Abstract, 37th Annual Meeting of Endocrine Society of India, Tirupati, A. P., India Esicon (2007) (2 pages).
"WMA Declaration of Helsinki—Ethical Principles for Medical Research Involving Human Subjects," 18th World Health Congress (Helsinki), WMA (1964) (8 pages).
Yki-Jarvinen, H. et al., "Insulin glargine or NPH combined with metformin in type 2 diabetes: the LANMET study," Diabetologia 49(3):44251 (2006).
International Search Report issued by the International Searching Authority for International Application No. PCT/ EP2010/067250; dated Mar. 23, 2011, pp. 1-3.
International Search Report issued by the International Searching Authority for International Application No. PCT/ EP2011/058079; dated Mar. 22, 2012, pp. 1-5.
Extended European Search Report issued by the European Patent Office for EP Application No. EP 14166877.2; dated Aug. 28, 2014, pp. 1-6.
Extended European Search Report issued by the European Patent Office for EP Application No. 11166415.7; dated Mar. 20, 2012, pp. 1-11.
Final Rejection issued in U.S. Appl. No. 13/382,772; mailed Jun. 3, 2014, pp. 1-34.
Non-Final Rejection issued in U.S. Appl. No. 13/382,772; mailed Sep. 29, 2014, pp. 1-33.
Final Rejection issued in U.S. Appl. No. 13/382,772; mailed Feb. 10, 2015, pp. 1-36.
Non-Final Rejection issued in U.S. Appl. No. 13/509,542; mailed May 23, 2013, pp. 1-21.
Final Rejection issued in U.S. Appl. No. 13/509,542; mailed Nov. 21, 2013, pp. 1-34.
Non-Final Rejection issued in U.S. Appl. No. 13/509,542; mailed Apr. 2, 2014, pp. 1-20.
Final Rejection issued in U.S. Appl. No. 13/509,542; mailed Jan. 28, 2015, pp. 1-26.
Non-Final Rejection issued in U.S. Appl. No. 14/220,562; mailed Apr. 8, 2015, pp. 1-18.
Brange & Langkjaer, "Insulin Structure and Stability" Chapter 11; Pharm Biotechnol 5:315-50 (1993).
Search Report of the Intellectual Property Corporation of Malaysia for Malaysian Patent Application No. PI 2011006204; dated Aug. 17, 2015, p. 1.
EMA—Science Medicines Health "Toujeo" EPAR Summary for the Public, first published Nov. 5, 2009, pp. 1-3.
Barnett & Owens, "Insulin Analogues," Lancet 349(9044):47-51 (1997).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Buse et al., "Use of twice-daily exenatide in Basal insulin-treated patients with type 2 diabetes: a randomized, controlled trial." Annals of Internal Medicine 154(2):103-12 (Jan. 2011).
Childs et al., "Defining and Reporting Hypoglycemia in Diabetes," Diabetes Care 28(5):1245-9 (May 2005).
Database, Adiscti, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Fox et al., Protein Science 10: 622-30 (2001).
Goykhman et al., "Insulin Glargine: a review 8 years after its introduction." Expert Opin. Pharmacother. 10(4):705-18 (2009).
Hartmann et al., "Biological Activity of des-(B26-B30)-Insulinamide and Related Analogues in Rat Hepatocyte Cultures," Diabetologia 32(7):416-20 (1989).
Jekel et al., "Use of endoproteinase Lys-C from Lysobacter enzymogenes in protein sequence analysis," Anal Biochem. 134(2):347-54 (1983).
Kielgast et al., "Treatment of type 1 diabetic patients with glucagon-like peptide-1 (GLP-1) and GLP-1R agonists." Curr Diabetes Rev. 5(4):266-75 (Nov. 2009).
Kohn et al., "pi-shifted insulin analogs with extended in vivo time action and favorable receptor selectivity," Peptide 28:935-48 (2007).
Leyer et al., "The role of the C-terminus of the insulin B-chain in modulating structural and functional properties of the hormone," Int J Pep Protein Res. 46(5):397-407 (1995).
Markussen et al., "Soluble, prolonged-acting insulin derivatives. I. Degree of protraction and crystallizability of insulins substituted in the termini of the B-chain," Prot. Eng. 1(3), 1987, pp. 205-213.
Markussen et al., "Soluble, prolonged-acting insulin derivatives. II. Degree of protraction and crystallizability of insulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Mikhail, "Is liraglutide a useful addition to diabetes therapy?" Endocr Practice 16(6):1028-37 (Nov.-Dec. 2010).
"Preferable." Merriam-Webster.com. Merriam-Webster, n.d. Web. Sep. 7, 2015. http://www.merriamwebster.com/dictionary/preferable).
Sanger et al., The amide groups of insulin, Biochem J. 59(3):509-18 (1955).
Sanofi Press Release entitled "FDA Accepts Sanofi's New Drug Application for Basal Insulin Toujeo®," dated Jul. 8, 2014, pp. 1-2.
Sanofi Press Release entitled "Sanofi Receives FDA Approval of Once-Daily Basal Insulin Toujeo®," dated Feb. 26, 2015, pp. 1-4.
Schellenberger et al., "Attempts for Quantifying the S' Subsite Specificity of Serine Proteases," Selected Papers Presented at the 2nd International Meeting on the Molecular and Cellular Regulation of Enzyme Activity, Advances in the Biosciences, Peptides and Proteases: Recent Advances 65:159-66 (1987).
Schellenberger et al., "Protease-Catalyzed Kinetically Controlled Peptide Synthesis," Angewante Chemie, International Edition 30(11):1437-49 (1991).
Starkova, ed., "Clinical Endocrinology", Guide for physicians, Moscow, "Medicine", 1991, p. 192-262 (English translation submitted).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Non-Final Rejection issued in U.S. Appl. No. 13/382,772; mailed Sep. 14, 2015, pp. 1-42.
Non-Final Rejection issued in U.S. Appl. No. 13/509,542; mailed Aug. 11, 2015, pp. 1-30.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.

(56) References Cited

OTHER PUBLICATIONS

International Search Report by the ISA for International Application No. PCT/EP2014/056498; dated Jun. 25, 2014, pp. 1-10.

Extended European Search Report for European Application No. 10 30 5780; dated Nov. 16, 2010, pp. 1-3.

Extended European Search Report for European Application No. 13 305 432.0; dated Sep. 13, 2013, pp. 1-5.

English translation of Search Report for Chinese Patent Application No. 20140220537.9; dated Feb. 13, 2015, pp. 1-2.

http://diabetes.emedtv.com/lantus/generic-lantus.html; one page, last accessed Dec. 23, 2015.

European Medicines Agency—Science Medicines Health, "Guideline on clinical investigation of medicinal products in the treatment of diabetes mellitus" Committee for Medicinal Products for Human Use, Jan. 20, 2010, pp. 1-19.

European Medicines Agency, "Toujeo (previously Optisulin) insulin glargine," <http://www.ema.europa.eu/ema/index.jsp?curl=pages/medicines/human/medicines/000309/human_med_000955.jsp&mid=WC0b01ac058001d124>, last updated Jan. 25, 2016, visited Feb. 3, 2016, pp. 1-6—screenshot of "About" tab of webpage and printouts of "About" tab of webpage with listed items collapsed and expanded.

Ex Parte Herrmann, Appeal No. 2009-001777 U.S. Appl. No. 10/616,457 (B. Pai. Nov. 13, 2009).

Jorgensen et al., "Five fold increase of insulin concentration delays the absorption of subcutaneously injected human insulin suspension in pigs", Diabetes Research and Clinical Practice, 50:161-167 (2000).

Kaarsholm et al., "Engineering stability of the insulin monomer fold with application to structure-activity relationships," Biochemistry 32(40):10773-8 (1993).

NCT01195454, NIH Clinical Trials, "Euglycemic clamp dose-response study comparing insulin glargine U300 with Lantus U100" last updated Dec. 13, 2010, pp. 1-4.

Request for "Type C" Meeting letter sent by Michael Lutz addressed to Mary Parks, dated Apr. 21, 2006, pp. 1-10.

Final Rejection issued in U.S. Appl. No. 13/382,772; mailed Feb. 24, 2016, pp. 1-36.

Final Rejection issued in U.S. Appl. No. 13/509,542, mailed Feb. 10, 2016, pp. 1-40.

English translation of the TIPO Search Report for ROC Patent Application No. 104116749, dated Feb. 22, 2016, one page.

U.S. Appl. No. 13/382,772, filed May 29, 2012, Schoettle.

U.S. Appl. No. 14/220,562, filed Mar. 20, 2014, Becker et al.

U.S. Appl. No. 13/123,835, filed Sep. 30, 2011, Werner et al.

U.S. Appl. No. 14/523,842, filed Oct. 24, 2014, Loos et al.

Nettleton et al. "Characterization of the Oligomeric States of Insulin in Self-Assembly and Amyloid Fibril Formation by Mass Spectrometry," Biophysical J., v79, 2000, p. 1053-1065.

Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).

Pi-Sunyer et al., "The effects of pharmacologic agents for type 2 diabetes mellitus on body weight". Postgrad Med. 120(2):5-17 (Jul. 2008).

RPMI-1640 Media Formulation, Sigma Aldrich, accessed on Jul. 10, 2016, pp. 1-5.

Russell-Jones, "Current developments in the treatment of diabetes: the incretin therapies" Br J Diabetes Vasc Dis. 10:21-30 (Feb. 2010).

Schwartz et al., "A superactive insulin: [B10-Aspartic acid]insulin(human)," Proc. Natl. Acad. Sci. USA, 84(18):6408-11 (Sep. 1987).

Sluzky et al., "Kinetics of Insulin Aggregation in Aqueous Solutions Upon Agitation in the Presence of Hydrophobic Surfaces," Proc. Natl. Acad. Sci. USA. 88(21):9377-81 (Nov. 1991).

Sundby "Separation and Characterization of Acid-Induced Insulin Transformation Products by Paper Electrophoresis in 7 M Urea," J. Biol. Chem. 237(11):3406-11 (Nov. 1962).

Tews et al., Abstract of Oral Presentation "Enhanced Protection Against Cytokine- and Fatty Acid-induced Apoptosis in Ins-1

Beta-Cells by Combined Treatment with Insulin Glargine and the Novel GLP-1 Receptor Agonist AVE0010" Diabetes, 56(Suppl. 1):A72-A73 (2007).

Thurow & Geisen, "Stabilisation of dissolved proteins against denaturation at hydrophobic interfaces," Diabetologia, 27(2):212-18 (Aug. 1984).

Volund et al., "In Vitro and In Vivo Potency of Insulin Analogues Designed for Clinical Use," Diab. Med. 8(9):839-47 (Nov. 1991).

Ward "Diabetic neuropathy," British Medical Bulletin, 45(1):111-26 (Jan. 1989).

Weyer et al., "Long-term changes in insulin action and insulin secretion associated with gain, loss, regain and maintenance of body weight", Diabetologia, (43)1:36-46 (Jan. 2000).

WHO Rational Use of Medicines,http://www.who.int/medicines/areas/rational_use/en/downloaded Dec. 18, 2014 10:02:48 AM (2012).

Zinman "The Physiologic Replacement of Insulin," New England J. Med. 321(6):363-70 (Aug. 1989).

Senstius et al., "Comparison of in vitro stability for insulin aspart and insulin glulisine during simulated use in insulin pumps." Diabetes Technol Ther. 9(6):517-21 (Dec. 2007).

Non-Final Rejection issued in U.S. Appl. No. 13/509,542; mailed Nov. 23, 2016, pp. 1-34.

International Search Report by the ISA for International Application No. PCT/EP2009/063195; dated May 6, 2010, one page.

Extended European Search Report from the European Patent Office for EP Application No. 13306475.8 dated Mar. 3, 2014, pp. 1-6.

International Search Report for International application No. PCT/EP2014/072915 mailed on Dec. 9, 2014, pp. 1-3.

Final Office Action issued in U.S. Appl. No. 13/123,835; mailed Nov. 18, 2015, pp. 1-16.

Non-Final Office Action issued in U.S. Appl. No. 13/123,835; mailed May 28, 2015, pp. 1-11.

Non-Final Office Action issued in U.S. Appl. No. 13/123,835; mailed Dec. 22, 2014, pp. 1-13.

Final Office Action issued in U.S. Appl. No. 13/123,835; mailed Feb. 12, 2013, pp. 1-13.

Non-Final Office Action issued in U.S. Appl. No. 13/123,835; mailed Jul. 19, 2012, pp. 1-14.

Rothstein et al., "Anticandida activity is retained in P-113, a 12-amino-acid fragment of histatin 5." Antimicrob Agents Chemother. 45(5):1367-73 (May 2001).

American Diabetes Association Annual Scientific Sessions, "New Diabetes Compound AVE0010 Showed Clear Dose Response Results With Once-A-Day Injection in Phase IIb Study", published Jun. 9, 2008, two pages.

Aoki et al., Hydrolysis of Nonionic Surfactants, Ann. Rept. Takeda Res. Lab. 27, 172-176 (1968).

Berger "Towards more physiological insulin therapy in the 1990s—A comment," Diabetes Research and Clinical Practice, 6(4): S25-31 (May 1989).

Bolli "The pharmacokinetic basis of insulin therapy in diabetes mellitus," Diabetes Research and Clinical Practice, 6(4):S3-15 (May 1989).

Brange & Langkjaer, "Chemical stability of insulin 3. Influence of excipients, formulation, and pH," Acta Pharma. Nord. 4(3):149-58 (1992).

Brange et al., "Monomeric insulins and their experimental and clinical implications," Diabetes Care 13(9):923-45 (Sep. 1990).

Brange et al., "Neutral insulin solutions physically stabilized by addition of Zn2+," Diabetic Medicine 3:532-6 (Nov.-Dec. 1986).

Brange "Galenics of Insulin" p. 35-36. (1987).

Burgermeister et al. "The Isolation of Insulin from the Pancreas," Insulin, Part 2, p. 715-727 (1975).

Burke et al., "Nature of the B10 amino acid residue," Int. J. Peptide Protein Res., 23(4):394-401 (Apr. 1984).

Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.

Dixon et al., "Regeneration of Insulin Activity From the Separated and Inactive A and B Chains," Nature, vol. 188, No. 4752 (1960), pp. 721-724.

Drury et al., "Diabetic nephropathy," British Medical Bulletin, vol. 45, No. 1, 1989, pp. 127-147.

(56) References Cited

OTHER PUBLICATIONS

FDA Frequently Asked Questions about Combination Products;accessed from www.fda.gov/CombinationProducts/AboutCombinationProducts/usm101496.1/htm, 2009 downloaded Jul. 13, 2012, pp. 1-18.

Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).

Geiger, Chem. Zeitung, 100(3), p. 54-56. (Jan. 1976).

GenBank: AAP20099.1 "Interferon Alpha 2B [*Homo sapiens*]" dated Apr. 30, 2003; accessed Jan. 18, 2017, one page.

GenBank: AAA59149.1 "Interleukin 4 [*Homo sapiens*]" dated Jan. 6, 1995; accessed Jan. 18, 2017, one page.

GenBank: AAA52578.1 "GM-CSF [*Homo sapiens*]" dated Nov. 8, 1994; accessed Jan. 18, 2017, one page.

Giacometti et al., "In vitro activity of the histatin derivative P-113 against multidrug-resistant pathogens responsible for pneumonia in immunocompromised patients." 49(3):1249-52 (Mar. 2005).

Hinds et al., "Synthesis and characterization of poly(ethylene glycol)-insulin conjugates." Bioconjugate Chem. 11(2):195-201 (Mar.-Apr. 2000).

Home et al., "Insulin treatment: a decade of change," British Medical Bulletin, 1989, vol. 45, No. 1, pp. 92-110.

Kadima "Role of Metal Ions in the T- to R-Allosteric Transition in the Insulin Hexamer," Biochem. 38(41):13443-53 (Oct. 1999).

Kang et al., "Subcutaneous Insulin Absorption Explained by Insulin's Physicochemical Properties-Evidence from Absorption Studies of Soluble Human Insulin and Insulin Analogues in Humans," Diabetes Care, 14(11):942-48 (Nov. 1991).

Kemmler et al., "Studies on the Conversion of Proinsulin to Insulin," The Journal of Biological Chemistry, 246(22):6786-91 (1971).

Kohner "Diabetic retinopathy," British Medical Bulletin, vol. 45, No. 1, 1989, pp. 148-173.

Lantus® Drug Description, downloaded Nov. 12, 2015, one page.

Lill, "Production of fast-acting insulins and delayed-release insulins—how can this problem be solved by technology? Insulin formulations," Pharmazie in unserer Zeit 30(1):56-61 (2001). (English Translation Included).

Lougheed et al., "Physical Stability of Insulin Formulations," Diabetes, 32(5):424-32 (May 1983).

Muller et al., "Insulin Signaling in the Yeast *Saccharomyces cerevisiae*. 1. Stimulation of Glucose Metabolism and Snf 1 Kinase by Human Insulin," Biochemistry, 37(24):8683-95 (Jun. 1998).

Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1):A258, Poster 1010-P (Jun. 2012).

Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).

Non-Final Office Action issued in U.S. Appl. No. 15/340,969; mailed Jul. 24, 2017, pp. 1-6.

Extended European Search Report for European Application No. 16 19 0103.8; dated Jun. 23, 2017, pp. 1-5.

FDA, "Guidance of Industry—Bioequivalence studies with pharmacokinetic endpoints for drugs submitted under an Anda" Draft Guidance by the U.S. Department of Health and Human Services, Food and Drug Administration, Center for Drug Evaluation and Research (CDER), Dec. 2013, pp. 1-24.

Gillies et al., "Insulin Glargine" Drugs 59(2)L253-60 (Feb. 2000).

Gualandi-Signorini & Giorgi, "Insulin formulations—a review" European Review for Medical and Pharmacological Sciences 5:73-83 (2001).

Lantus® 100U/ml solution for injection (insuline glargine); published in vol. 24 No. 9 of Pract. Diab. Int. Nov./Dec. 2007, p. 472.

NCT01195454, NIH Clinical Trials, "Euglycemic clamp dose-response study comparing insulin glargine U300 with Lantus U100" last updated Sep. 3, 2010, pp. 1-3.

Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.

Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).

Shi, "The Newest Handbook of Clinical Drugs" Military Medical Science Press, p. 809, (Jan. 2008). English translation submitted.

Search Report in Chinese Patent Application No. 201410818149.0; dated Jan. 10, 2017, pp. 1-3. English translation submitted.

Tang, "Biotech Drugs—Introduction and Practice Handbook" Chemical Industry Press, pp. 635-636, (Jan. 2008). English translation submitted.

Search Report of the Intellectual Property Office of Singapore for Patent Application No. 10201403840V; search completed Nov. 21, 2017, pp. 1-3.

U.S. Appl. No. 15/340,969, filed Nov. 1, 2016, Werner et al.

Non-Final Rejection issued in U.S. Appl. No. 14/624,575; mailed Mar. 26, 2015, pp. 1-14.

Adis R&D Profile "Insulin Glargine: Glargine, HOE 71GT15, HOE 71GT80, HOE 901", Drugs R&D 2(2):107-109 (Aug. 1999).

Ashford & Landi, "Stabilizing Properties of Tween 80 in Dilute Protein Solutions" Bull Parenteral Drug Assoc. 20(3):74-84 (May-Jun. 1966).

Aventis SEC Form 20-F; pp. 1-303 (Apr. 8, 2002).

Bam et al., "Tween protects recombinant human growth hormone against agitation-induced damage via hydrophobic Interactions" J. Ph. Sci. 87(12):1554-59 (Dec. 1998).

Bam et al., "Stability of Protein Formulations: Investigation of Surfactant Effects by a Novel EPR Spectroscopic Technique," Pharmaceutical Research, 12(1):2-11 (Jan. 1995).

Bates et al., "Kinetics of hydrolysis of polyoxyethylene (20) sorbitan fatty acid ester surfactants," J. Pharmacy and Pharmacology 25(6):470-77 (Jun. 1973).

Berchtold & Hilgenfeld, "Binding of Phenol to R6 Insulin Hexamers" Biopolymers 51(2):165-72 (1999).

Chawla et al., "Aggregation of Insulin, Containing Surfactants, in Contact with Different Materials", Diabetes 34(5):420-24 (May 1985).

Derewenda et al., "Phenol Stabilizes More Helix in a New Symmetrical Zinc Insulin Hexamer" Nature 338(6216):594-96 (Apr. 1989).

Drug Facts and Comparison; J. B. Lippincot Company, St. Louis, MO; pp. 1781-1790 (1988).

EMEA Public Statement on Insuman Infusat (Feb. 14, 2000), at http://www.ema.europa.eu/ema/index.jsp?curl=pages/news_and_events/news/2010/08/news_detail_001094.jsp&mid=WC0b01ac058004d5c1 (accessed Jun. 1, 2017); pp. 1-2.

Excerpts from "Handbook of Pharmaceutical Excipients" 2nd Edition (eds. A. Wade and P.J. Weller) American Pharmaceutical Association, Washington, The Pharmaceutical Press, London; pp. 1-55 (1994).

Gatlin & Gatlin, "Formulation and Administration Techniques to Minimize Injection Pain and Tissue Damage Associated with Parenteral Products" in Injectable Drug Development, Chapter 17; pp. 401-421 (eds. P.K. Gupta and G.A. Brazeau) (CRC Press) (1999).

Grau & Saudek, "Stable Insulin Preparation for Implanted Insulin Pumps", Diabetes 36(12):1453-59 (Dec. 1987).

Hallas-Moller, "The Lente Insulins", Diabetes 5:7-14 (Jan.-Feb. 1956).

Heile & Schneider, "The Evolution of Insulin Therapy in Diabetes Mellitus", J Fam Pract 61(5 Suppl.):S6-12 (May 2012).

Insuman Infusat entry in Rote Liste, one page (2001).

Insuman Infusat; Fass Entry for Insuman Infusat; pp. 1-6 (Jan. 2000). English translation of Jun. 5, 2017, pp. 1-8 also submitted.

Jones, "Insulin Glargine Aventis Pharma", IDrugs 3(9):1081-87 (Sep. 2000).

Jones et al. "Surfactant-Stabilized Protein Formulations: A Review of Protein-Surfactant interactions and Novel Analytical Methodolo-

(56) References Cited

OTHER PUBLICATIONS gies," Therapeutic Protein & Peptide Delivery, ACS Symposium Series; Chapter 12, pp. 206-222 (1997).

Katakam et al., "Effect of Surfactants on the Physical Stability of Recombinant Human Growth Hormone" J Pharm Sci 84(6):713-16 (Jun. 1995).

Lantus® entry in Physician's Desk Reference; pp. 1-6 (2001).

Lantus®—FDA Drug Approval Letter for Lantus® (NDA 02-1081) at https://www.accessdata.fda.gov/scripts/cder/daf/index.cfm?event=overview.process&ApplNo=021081 (accessed Jan. 25, 2018), pp. 1-5.

Lantus®—FDA Drug Approval Label for Lantus® (NDA 02-1081) (Apr. 20, 2000) at https://www.accessdata.fda.gov/scripts/cder/daf/index.cfm?event=overview.process&ApplNo=021081 (accessed Jan. 25, 2018), pp. 1-14.

Lee et al., "Effect of Brij-78 on Systemic Delivery of Insulin from an Ocular Device" J Pharm Sci 86(4):430-33 (Apr. 1997).

Lee et al., "Review on the Systemic Delivery of Insulin via the Ocular Route" Int'l J Pharmaceutics 233(1-2):1-18 (Feb. 2002).

Lougheed et al., "Insulin Aggregation in Artificial Delivery Systems" Diabetologia 19(1):1-9 (Jul. 1980).

Manning et al., "Stability of Protein Pharmaceuticals," Pharm Research, 6(11):903-18 (Nov. 1989).

McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).

Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).

Schmolka, "Poloxamers in the Pharmaceutical Industry" in Polymers for Controlled Drug Delivery, Chapter 10, pp. 189-214 (CRC Press) (1991).

Soeborg et al., "Absorption kinetics of insulin after subcutaneous administration" European Journal of Pharmaceutical Sciences 36(1):78-90 (Jan. 2009; Epub Nov. 5, 2008).

Soliqua® Product Information; pp. 1-33 (Oct. 2017).

Soliqua® Consumer Medicine Information (CMI); pp. 1-7 (Oct. 2017).

Soliqua® Summary of Product Characteristics; pp. 1-74 (Jan. 2017).

Wang, "Instability, Stabilization and Formulation of Liquid Protein Pharmaceuticals," Int'l J Pharm, 185(2):129-88 (Aug. 1999).

Final Rejection issued in U.S. Appl. No. 15/162,563; mailed Apr. 17, 2018, pp. 1-16.

Non-Final Rejection issued in U.S. Appl. No. 15/162,563; mailed Feb. 8, 2017, pp. 1-13.

Final Rejection issued in U.S. Appl. No. 15/162,563; mailed Aug. 9, 2017, pp. 1-13.

Final Rejection issued in U.S. Appl. No. 15/162,563; mailed Dec. 18, 2017, pp. 1-16.

Bettley, "The Toxicity of Soaps and Detergents" Br. J. Derm., 80:635-642 (1968).

Lantus®—Prescribing Information as of Apr. 2000, pp. 1-16 (accessed from web archive dated Jan. 10, 2001).

Shao et al., "Differential Effects of Anionic, Cationic, Nonionic and Physiologic Surfactants on the Dissociation, alpha-Chymotryptic Degradation, and Enteral Absorption of Insulin Hexamers," Pharmaceutical Research, 10(2):243-251 (1993).

Strickley, "Review Article: Solubilizing Excipients in Oral and Injectable Formulations," Pharmaceutical Research 21(2):201-230 (Feb. 2004).

Tomizawa & Kondo, "Mechanism of hemolysis by anionic surface-active agents," Kolloid-Z. u. Z. Polymere 246:694-99 (1971).

Final Rejection issued in U.S. Appl. No. 15/162,563; mailed Oct. 1, 2018, pp. 1-16.

Non-Final Rejection issued in U.S. Appl. No. 16/108,064; mailed Mar. 18, 2019, pp. 1-17.

English translation of Search Report for Chinese Patent Application No. 201710022418.6 ; dated Mar. 16, 2020, pp. 1-2.

Byetta® Product information—EMA, pp. 1-2 (Jun. 10, 2016).

Dunn et al., "Insulin Glargine: An Updated Review of its Use in the Management of Diabetes Mellitus" Drugs 63(16):1743-1778 (2003).

European Public Assessment Report (EPAR) Optisulin EPAR summary for the public. Last updated Feb. 2009; pp. 1-3. (submitted as Exhibit A on Mar. 10, 2016).

Merck Index, "Metformin", The Merck Index, 15th Edition (2013), RSC Publishing, 4 pages submitted, p. 1102.

Tang, "Biotech Drugs—Introduction and Practice Handbook" Chemical Industry Press, pp. 635-642 (Jan. 2008). English translation submitted.

Wikipedia® entry for "Insulin product" Retrieved from the Internet: (more info needed), dated Feb. 21, 2020.

Non-Final Rejection issued in U.S. Appl. No. 13/509,507; mailed Aug. 6, 2013, pp. 1-11.

Non-Final Rejection issued in U.S. Appl. No. 13/509,507; mailed Sep. 19, 2014, pp. 1-9.

Non-Final Rejection issued in U.S. Appl. No. 13/509,507; mailed Feb. 19, 2015, pp. 1-10.

Final Rejection issued in U.S. Appl. No. 13/509,507; mailed Jul. 23, 2015, pp. 1-11.

Non-Final Rejection issued in U.S. Appl. No. 13/509,507; mailed Dec. 8, 2015, pp. 1-14.

Final Rejection issued in U.S. Appl. No. 13/509,507; mailed May 13, 2016, pp. 1-11.

Non-Final Rejection issued in U.S. Appl. No. 13/509,507; mailed Sep. 21, 2016, pp. 1-7.

Final Rejection issued in U.S. Appl. No. 16/368,201; mailed Nov. 14, 2019, pp. 1-17.

International Search Report by the ISA for International Application No. PCT/EP2010/067249; dated Feb. 4, 2011, pp. 1-3.

Written Opinion of the ISA for International Application No. PCT/EP2011/058079, mailed Mar. 22, 2012, pp. 1-8.

Extended European Search Report from European Application No. EP 14 16 6877.2; dated Aug. 28, 2014, pp. 1-6.

Extended European Search Report from European Application No. EP 18 15 5758; dated Oct. 15, 2018, pp. 1-4.

International Search Report and Written Opinion dated Jun. 17, 2011 received from the European Patent Office from related Application No. PCT/EP2010/059436.

Office Action dated Oct. 25, 2012 received from the European Patent Office from related Application No. 10 730 443.8.

English-language abstract Schubert-Zsilavecz M. et al., "Better Blood Glucose Levels in Diabetics-Insulin Glargin—A Long-Acting Insulin Analog", *Pharmazie in Unserer Zeit* pp. 125-130 (2001).

English-language translation of International Search Report dated Oct. 4, 2010 received from the European Patent Office from related International Application No. PCT/EP2010/059438.

* cited by examiner

INSULIN PREPARATIONS CONTAINING METHIONINE

CROSS-REFERENCE TO RELATED APPLICATIONS

This application claims the benefit of U.S. Provisional Application No. 61/264,356 filed on Nov. 25, 2009.

The invention relates to an aqueous pharmaceutical formulation with an insulin, insulin analog or insulin derivative, and methionine; and also to its preparation, use for treating diabetes mellitus, and to a medicament for treating diabetes mellitus.

An increasing number of people around the world suffer from diabetes mellitus. Many of them are what are called type I diabetics, for whom replacement of the deficient endocrine insulin secretion is the only possible therapy at present. Those affected are dependent on insulin injections for life, usually several times a day. Type II diabetes contrasts with type I diabetes in that there is not always a deficiency of insulin, but in a large number of cases, especially at the advanced stage, treatment with insulin, where appropriate in combination with an oral antidiabetic, is considered the most advantageous form of therapy.

In healthy individuals, release of insulin by the pancreas is strictly coupled to the blood glucose concentration. Elevated blood glucose levels, like those occurring after meals, are quickly compensated by a corresponding rise in insulin secretion. In the fasting state, the plasma insulin level falls to a base line value which is sufficient to ensure a continuous supply of glucose to insulin-sensitive organs and tissues, and to keep hepatic glucose production low in the night. The replacement of the endogenous insulin secretion by exogenous, usually subcutaneous administration of insulin does not in general come close to the above-described quality of the physiological regulation of blood glucose. Frequently there are instances of blood glucose being thrown off-track, either upwardly or downwardly, and in their most severe forms these instances may be life-threatening. In addition, however, blood glucose levels which are elevated over years, without initial symptoms, constitute a considerable health risk. The large-scale DCCT study in the USA (The Diabetes Control and Complications Trial Research Group (1993), N. Engl. J. Med. 329, 977-986) showed unambiguously that chronically elevated blood glucose levels are responsible for the development of late diabetic complications. Late diabetic complications are microvascular and macrovascular damage which is manifested in certain circumstances as retinopathy, nephropathy, or neuropathy, and leads to blindness, renal failure, and loss of extremities, and, in addition, is associated with an increased risk of cardiovascular disorders. From this it can be inferred that an improved therapy of diabetes must be aimed primarily at keeping blood glucose as closely as possible within the physiological range. According to the concept of intensified insulin therapy, this is to be achieved by means of injections, several times a day, of fast-acting and slow-acting insulin preparations. Fast-acting formulations are given at meal times, in order to compensate the postprandial rise in blood glucose. Slow-acting basal insulins are intended to ensure the basic supply of insulin, especially during the night, without leading to hypoglycemia.

Insulin is a polypeptide composed of 51 amino acids which are divided between two amino acid chains: the A chain, with 21 amino acids, and the B chain, with 30 amino acids. The chains are linked together by two disulfide bridges. Insulin preparations have been employed for many years in diabetes therapy. Such preparations use not only naturally occurring insulins but also, more recently, insulin derivatives and insulin analogs.

Insulin analogs are analogs of naturally occurring insulins, namely human insulin or animal insulins, which differ by replacement of at least one naturally occurring amino acid residue by other amino acids and/or by addition/deletion of at least one amino acid residue, from the corresponding, otherwise identical, naturally occurring insulin. The amino acids in question may also be amino acids which do not occur naturally.

Insulin derivatives are derivatives of naturally occurring insulin or an insulin analog which are obtained by chemical modification. The chemical modification may consist, for example, in the addition of one or more defined chemical groups to one or more amino acids. Generally speaking, the activity of insulin derivatives and insulin analogs is somewhat altered as compared with human insulin.

Insulin analogs with an accelerated onset of action are described in EP 0 214 826, EP 0 375 437, and EP 0 678 522. EP 0 214 826 relates, among other things, to replacements of B27 and B28. EP 0 678 522 describes insulin analogs which have different amino acids in position B29, preferably proline, but not glutamic acid. EP 0 375 437 encompasses insulin analogs with lysine or arginine at B28, which may also optionally be modified at B3 and/or A21.

EP 0 419 504 discloses insulin analogs which are protected from chemical modifications by modification of asparagine in B3 and of at least one further amino acid at positions A5, A15, A18 or A21.

Generally speaking, insulin derivatives and insulin analogs have a somewhat altered action as compared with human insulin.

WO 92/00321 describes insulin analogs in which at least one amino acid in positions B1-B6 has been replaced by lysine or arginine. Such insulins, according to WO 92/00321, have an extended effect. A delayed effect is also exhibited by the insulin analogs described in EP-A 0 368 187. The concept of intensified insulin therapy attempts to reduce the risk to health by aiming for stable control of the blood sugar level by means of early administration of basal insulins. One example of a common basal insulin is the drug Lantus® (active ingredient: insulin glargine=Gly (A21), Arg (B31), Arg (B32) human insulin). Generally speaking, the aim in the development of new, improved basal insulins is to minimize the number of hypoglycemic events. An ideal basal insulin acts safely in each patient for at least 24 hours. Ideally, the onset of the insulin effect is delayed and has a fairly flat time/activity profile, thereby significantly minimizing the risk of short-term undersupply of sugar, and allowing administration even without food being taken beforehand. The supply of basal insulin is effective when the insulin activity goes on consistently for as long as possible, i.e., the body is supplied with a constant amount of insulin. As a result, the risk of hypoglycemic events is low, and patient-specific and day-specific variability are minimized. The pharmacookinetic profile of an ideal basal insulin, then, ought to be characterized by a delayed onset of action and by a delayed action, i.e., a long-lasting and uniform action.

The preparations of naturally occurring insulins for insulin replacement that are present on the market differ in the origin of the insulin (e.g., bovine, porcine, human insulin) and also in their composition, and so the activity profile (onset and duration of action) may be affected. Through combination of different insulin products it is possible to obtain any of a very wide variety of activity profiles and to bring about very largely physiological blood sugar values. Recombinant DNA technology nowadays allows the preparation of modified insulins of this kind. They include insulin glargine (Gly(A21)-Arg(B31)-Arg(B32) human insulin), with an extended duration of action. Insulin glargine is injected in the form of a clear, acidic solution, and, on the basis of its dissolution properties is precipitated, in the physiological pH range of the subcutaneous tissue, as a stable hexamer association. Insulin glargine is injected once a day and is notable in comparison with other long-active insulins for its flat serum profile and the associated reduction in the risk of night hypoglycemias (Schubert-Zsilavecz et al., 2:125-130 (2001)). In contrast to preparations described to date, the specific preparation of insulin glargine that leads to the prolonged duration of action is characterized by a clear solution with an acidic pH. Specifically at acidic pH, however, insulins exhibit reduced stability and an increased tendency toward aggregation under thermal and physico-mechanical load, which may be manifested in the form of haze and precipitation (particle formation) (Brange et al., J. Ph. Sci 86:517-525 (1997)).

It has been found that such insulin analogs lead to the described desired basal time/activity profile, when the insulin analogs are characterized by the features that the B chain end is composed of an amidated basic amino acid residue such as lysine or arginine amide, i.e., in the amidated basic amino acid residue at the B chain end, the carboxyl group of the terminal amino acid is in its amidated form, and molecular processes that may occur, affecting the insulins, insulin analogs and insulin derivatives, that are deleterious to the quality of the formulation. One substance which impairs the chemical stability of insulins, insulin analogs, and insulin derivatives is oxygen, whose contact with the formulations in question is unavoidable, owing to its presence in the air—particularly in the case of formulations in packs for multiple administration. It is assumed that, among other things, it is the oxidative potential of oxygen that brings about the impairments in chemical stability.

It has now been found that, surprisingly, the addition of the amino acid methionine to formulations of insulins, insulin analogs, and insulin derivatives leads to an improved stability on the part of these proteins.

The invention accordingly provides an aqueous, pharmaceutical formulation comprising an insulin, insulin analog or insulin derivative, or a pharmacologically tolerable salt thereof, and methionine.

The invention further provides a pharmaceutical formulation as described above, the insulin being selected from a group containing human insulin, porcine insulin, and bovine insulin.

The invention further provides a pharmaceutical formulation as described above, the insulin analog being selected from the group containing Gly(A21), Arg(B31), Arg(B32) human insulin, Lys(B3). Glu(B29) human insulin, Asp(B28) human insulin, Lys(B28) Pro(B29) human insulin. Des(B30) human insulin and an insulin analog of the formula I (SEQ ID NO: 1)

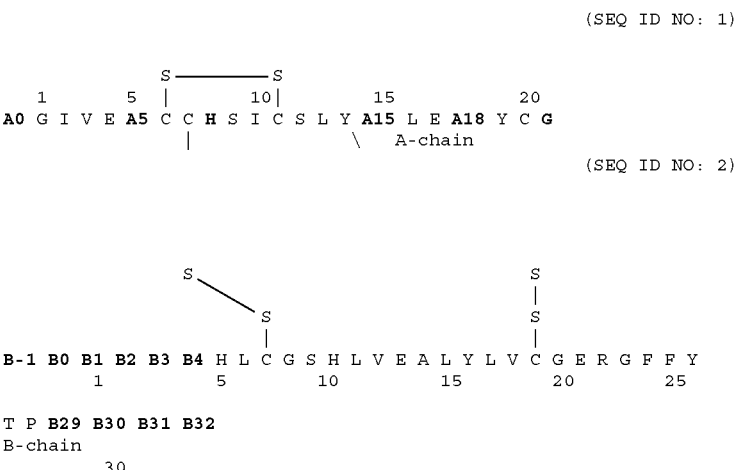

(SEQ ID NO: 2)

the N-terminal amino acid residue of the insulin A chain is a lysine or arginine residue, and the amino acid position A8 is occupied by a histidine residue, and the amino acid position A21 is occupied by a glycine residue, and there are two replacements of neutral amino acids by acidic amino acids, two additions of negatively charged amino acid residues, or one such replacement and one such addition, in each of positions A5, A15, A18, B-1, B0, B1, B2, B3, and B4.

Common to all aqueous formulations of insulins, insulin analogs, and insulin derivatives is that the stated proteins are not entirely stable chemically, but instead, as a function of the time, storage temperature, and movement to which the formulation is subject, and many more, there are a range of where
A0 is Lys or Arg;
A5 is Asp, Gln or Glu;
A15 is Asp, Glu or Gln;
A18 is Asp, Glu or Asn;
B-1 is Asp, Glu or an amino group;
B0 is Asp, Glu or a chemical bond;
B1 is Asp, Glu or Phe;
B2 is Asp, Glu or Val;
B3 is Asp, Glu or Asn;
B4 is Asp, Glu or Gln;
B29 is Lys or a chemical bond;
B30 is Thr or a chemical bond;
B31 is Arg, Lys or a chemical bond;
B32 is Arg-amide, Lys-amide or an amino group,
where two amino acid residues of the group containing
A5, A15, A18, B-1, B0, B1, B2, B3, and B4, simultaneously and independently of one another, are Asp or Glu, in particular in which the insulin analog is selected from a group containing:

Arg (A0), His (A8), Glu (A5), Asp (A18), Gly (A21), Arg (B31), Arg (B32)-NH₂ human insulin, Arg (A0), His (A8), Glu (A5), Asp (A18), Gly (A21), Arg (B31), Lys (B32)-NH₂ human insulin, Arg (A0), His (A8), Glu (A15), Asp (A18), Gly (A21), Arg (B31), Arg (B32)-NH₂ human insulin, Arg (A0), His (A8), Glu (A15), Asp (A18), Gly (A21), Arg (B31), Lys (B32)-NH₂ human insulin, Arg (A0), His (A8), Glu(A5), Glu (A15), Gly (A21), Arg (B31), Arg (B32)-NH₂ human insulin, Arg (A0), His (A8), Glu (A5), Glu (A15), Gly (A21), Arg (B31), Lys (B32)-NH₂ human insulin, Arg (A0), His(A8), Glu (A5), Gly (A21), Asp (B3), Arg (B31), Arg (B32)-NH₂ human insulin, Arg (A0), His(A8), Glu (A5), Gly (A21), Asp (B3), Arg (B31), Lys (B32)-NH₂ human insulin, Arg (A0), His (A8), Glu (A15), Gly (A21), Asp (B3), Arg (B31), Arg (B32)-NH₂ human insulin, Arg (A0), His (A8), Glu (A15), Gly (A21), Asp (B3), Arg (B31), Lys (B32)-NH₂ human insulin, Arg (A0), His (A8), Asp (A18), Gly (A21), Asp (B3), Arg (B31), Arg (B32)-NH₂ human insulin, Arg (A0), His (A8), Asp (A18), Gly (A21), Asp (B3), Arg (B31), Lys (B32)-NH₂ human insulin,

6

Arg (A0), His (A8), Asp (A18), Gly (A21), Glu (B0), Arg (B31), Lys (832)-NH₂ human insulin, Arg (A0), His (A8), Glu (A5), Gly (A21), Asp (B1), Arg (B31), Arg (B32)-NH₂ human insulin, Arg (A0), His (A8), Glu (A5), Gly (A21), Asp (B1), Arg (B31), Lys (B32)-NH₂ human insulin, Arg (A0), His (A8), Glu (A15), Gly (A21), Asp (B1), Arg (B31), Arg(B32)-NH₂ human insulin, Arg (A0), His (A8), Glu (A15), Gly (A21), Asp (B1), Arg (B31), Lys (B32)-NH₂ human insulin, Arg (A0), His (A8), Asp (A18), Gly (A21), Asp (B1), Arg (B31), Arg (B32)-NH₂ human insulin, Arg (A0), His (A8), Asp (A18), Gly (A21), Asp (B1), Arg (B31), Lys (B32)-NH₂ human insulin, Arg (A0), His (A8), Gly (A21), Glu (B0), Asp (B1), Arg (B31), Arg (B32)-NH₂ human insulin, Arg (A0), His (A8), Gly (A21), Glu (B0), Asp (B1), Arg (B31), Lys (832)-NH₂ human insulin, Arg (A0), His (A8), Asp (A18), Gly (A21), Asp (B3), Arg (B30), Arg (B31)-NH₂ human insulin, Arg (A0), His (A8), Asp (A18), Gly (A21), Asp (B3), Arg (B30), Lys (B31)-NH₂ human insulin.

The invention further provides a pharmaceutical formulation as described above, the insulin analog being selected from a group containing an insulin analog of the formula II

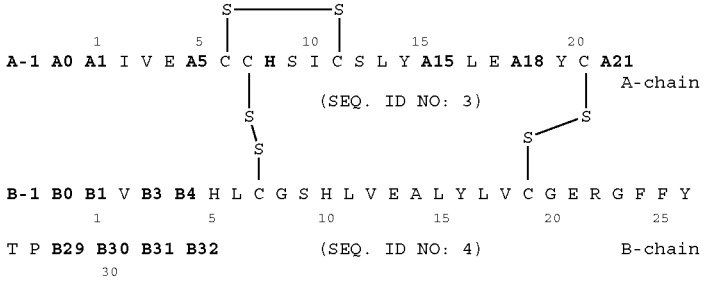

where

A-1 is Lys, Arg or an amino group;

A0 is Lys, Arg or a chemical bond;

A1 is Arg or Gly;

A5 is Asp, Glu or Gln;

A15 is Asp, Glu or Gln;

A18 is Asp, Glu or Asn;

A21 is Ala, Ser, Thr or Gly;

B-1 is Asp, Glu or an amino group;

B0 is Asp, Glu or a chemical bond;

B1 is Asp, Glu, Phe or a chemical bond;

B3 is Asp, Glu or Asn;

B4 is Asp, Glu or Gln;

B29 is Arg, Lys or an amino acid selected from the group containing the amino acids Phe, Ala, Thr, Ser, Val, Leu, Glu or Asp, or a chemical bond;

B30 is Thr or a chemical bond;

B31 is Arg, Lys or a chemical bond;

B32 is Arg-amide or Lys-amide, where not more than one amino acid residue from the group containing A5, A15, A18, B-1, B0, B1, B2, B3 and B4, simultaneously and independently of one another, is Asp or Glu, in particular in which the insulin analog is selected from a group containing:

Arg (A-1), Arg (A0), Glu (A5), His (A8), Gly (A21), Arg (B30)-NH₂ human insulin, Arg (A0), His(A8), Gly (A21), Asp (B3), Glu (B4), Arg (B31), Arg (B32)-NH₂ human insulin, Arg (A0), His (A8), Gly (A21), Asp (B3), Glu (B4), Arg (B31), Lys (B32)-NH₂ human insulin, Arg (A0), His (A8), Glu (A5), Gly (A21), Glu (B4), Arg (B31), Arg (B32)-NH₂ human insulin, Arg (A0), His (A8), Glu (A5), Gly (A21), Glu (B4), Arg (B31), Lys (B32)-NH₂ human insulin, Arg (A0), His (A8), Glu (A15), Gly (A21), Glu (B4), Arg (831), Arg (832)-NH₂ human insulin, Arg (A0), His (A8), Glu (A15), Gly (A21), Glu (B4), Arg (B31), Lys (B32)-NH₂ human insulin, Arg (A0), His (A8), Asp (A18), Gly (A21), Glu (B4), Arg (B31), Arg (B32)-NH₂ human insulin, Arg (A0), His (A8), Asp (A18), Gly (A21), Glu (B4), Arg (B31), Lys (B32)-NH₂ human insulin, Arg (A0), His (A8), Glu (A5), Gly (A21), Glu (B0), Arg (B31), Arg (B32)-NH₂ human insulin, Arg (A0), His (A8), Glu (A5), Gly (A21), Glu (B0), Arg (B31), Lys (B32)-NH₂ human insulin, Arg (A0), His (A8), Glu (A15), Gly (A21), Glu (B0), Arg (B31), Arg (B32)-NH₂ human insulin, Arg (A0), His (A8), Glu (A15), Gly (A21), Glu (B0), Arg (B31), Lys (B32)-NH₂ human insulin, Arg (A0), His (A8), Asp (A18), Gly (A21), Glu (B0), Arg (B31), Arg (B32)-NH₂ human insulin, Arg (A-1), Arg (A0), Glu (A5), His (A8), Gly (A21), Lys (B30)-NH$_2$ human insulin, Arg (A-1), Arg (A0), Glu (A15), His (A8), Gly (A21), Arg (B30)-NH$_2$ human insulin, Arg (A-1), Arg (A0), Glu (A15), His (A8), Gly (A21), Lys (B30)-NH$_2$ human insulin, Arg (A-1), Arg (A0), Asp (A18), His (A8), Gly (A21), Arg (B30)-NH$_2$ human insulin, Arg (A-1), Arg (A0), Asp (A18), His (A8), Gly (A21), Arg (B30)-NH$_2$ human insulin, Arg (A-1), Arg (A0), His (A8), Gly (A21), Glu (B0), Arg (B30)-NH$_2$ human insulin, Arg (A-1), Arg (A0), His (A8), Gly (A21), Glu (B0), Lys (B30)-NH$_2$ human insulin, Arg (A-1), Arg (A0), His (A8), Gly (A21), Asp (B3), Arg (B30)-NH$_2$ human insulin, Arg (A-1), Arg (A0), His (A8), Gly (A21), Asp (B3), Lys (B30)-NH$_2$ human insulin, Arg (A-1), Arg (A0), His (A8), Gly (A21), Glu (B4), Arg (B30)-NH$_2$ human insulin, Arg (A-1), Arg (A0), His (A8), Gly (A21), Glu (B4), Lys (B30)-NH$_2$ human insulin, Arg (A0), His (A8), Gly (A21), Arg (B31), Arg (B32)-NH$_2$ human insulin, Arg (A0), His (A8), Gly (A21), Arg (B31), Lys (B32)-NH$_2$ human insulin, Arg (A0), Glu (A5), His (A8), Gly (A21), Arg (B31), Arg (B32)-NH$_2$ human insulin, Arg (A0), Glu (A5), His (A8), Gly (A21), Arg (B31), Lys (B32)-NH$_2$ human insulin, Arg (A0), Asp (A18), His (A8), Gly (A21), Arg (B31), Arg (B32)-NH$_2$ human insulin, Arg (A0), Asp (A18), His (A8), Gly (A21), Arg (B31), Lys (B32)-NH$_2$ human insulin, Arg (A0), Glu (A15), His (A8), Gly (A21), Arg (B31), Arg (B32)-NH$_2$ human insulin, Arg (A0), Glu (A15), His (A8), Gly (A21), Arg (B31), Lys (B32)-NH$_2$ human insulin, Arg (A0), His (A8), Gly (A21), Asp (B3), Arg (B31), Arg (B32)-NH$_2$ human insulin, Arg (A0), His (A8), Gly (A21), Asp (83), Arg (B31), Lys (B32)-NH$_2$ human insulin, Arg (A0), His (A8), Gly (A21), Glu (B4), Arg (B31), Arg (B32)-NH$_2$ human insulin, Arg (A0), His (A8), Gly (A21), Glu (B4), Arg (B31), Lys (B32)-NH$_2$ human insulin, Arg (A0), His (A8), Gly (A21), Glu (B0), Arg (B31), Arg (B32)-NH$_2$ human insulin, Arg (A0), His (A8), Gly (A21), Glu (B0), Arg (B31), Lys (B32)-NH$_2$ human insulin, Arg (A0), His (A8), Gly (A21), Arg (B30)-NH$_2$ human insulin, Arg (A0), His (A8), Gly (A21), Lys (B30)-NH$_2$ human insulin, Arg (A-1), Arg (A0), His (A8), Gly (A21), Arg (B30)-NH$_2$ human insulin, Arg (A-1), Arg (A0), His (A8), Gly (A21), Lys (B30)-NH$_2$ human insulin, Arg (A0), Arg (A1), His (A8), Gly (A21), Arg (B30)-NH$_2$ human insulin, Arg (A0), Arg (A1), His (A8), Gly (A21), Lys (B30)-NH$_2$ human insulin, His (A8), Gly (A21), Arg (B31), Arg (B32)-NH$_2$ human insulin.

The invention further provides a pharmaceutical formulation as described above, the insulin derivative being selected from the group containing B29-N-myristoyl-des (B30) human insulin, B29-N-palmitoyl-des(B30) human insulin, B29-N-myristoyl human insulin. B29-N-palmitoyl human insulin, B28-N-myristoyl Lys$^{B28}$Pro$^{B29}$ human insulin, B28-N-palmitoyl-Lys$^{B28}$Pro$^{B29}$ human insulin, B30-N-myristoyl-Thr$^{B29}$Lys$^{B30}$ human insulin, B30-N-palmitoyl-Thr$^{B29}$Lys$^{B39}$ human insulin, B29-N—(N-palmitoyl-Y-glutamyl)-des(B39) human insulin. B29-N—(N-lithocholyl-Y-glutamyl)-des(B30) human insulin. B29-N-(ω-carboxyheptadecanoyl)-des(B30) human insulin, and B29-N-(ω-carboxy-heptadecanoyl) human insulin.

The invention further provides a pharmaceutical formulation as described above, comprising 0.001 to 0.2 mg/ml of zinc, 0.1 to 5.0 mg/ml of a preservative, and 5.0 to 100 mg/ml of an isotonicity agent, and having a pH of 5 or less.

The invention further provides a pharmaceutical formulation as described above, comprising a preservative selected from a group containing phenol, m-cresol, chlorocresol, benzyl alcohol, and parabens.

The invention further provides a pharmaceutical formulation as described above, comprising an isotonicity agent selected from a group containing mannitol, sorbitol, lactose, dextrose, trehalose, sodium chloride, and glycerol.

The invention further provides a pharmaceutical formulation as described above, having a pH in the range of pH 2.5-4.5, preferably pH 3.0-4.0, more preferably in the region of pH 3.75.

The invention further provides a pharmaceutical formulation as described above, the insulin, insulin analog and/or insulin derivative being present in a concentration of 240-3000 nmol/ml.

The invention further provides a pharmaceutical formulation as described above, comprising glycerol at a concentration of 20 to 30 mg/ml.

The invention further provides a pharmaceutical formulation as described above, comprising glycerol at a concentration of 25 mg/ml.

The invention further provides a pharmaceutical formulation as described above, comprising m-cresol at a concentration of 1 to 3 mg/ml, preferably 2 mg/ml.

The invention further provides a pharmaceutical formulation as described above, comprising zinc at a concentration of 0.01 or 0.03 or 0.08 mg/ml.

The invention further provides a pharmaceutical formulation as described above, further comprising a glucagon-like peptide-1 (GLP1) or an analog or derivative thereof, or exendin-3 and/or -4 or an analog or derivative thereof, preferably exendin-4.

The invention further provides a pharmaceutical formulation as described above, in which an analog of exendin-4 is selected from a group containing H-desPro$^{36}$-exendin-4-Lys$_6$-NH$_2$, H-des(Pro$^{36,37}$)-exendin-4-Lys$_4$-NH$_2$ and H-des(Pro$^{36,37}$)-exendin-4-Lys$_5$-NH$_2$, or a pharmacologically tolerable salt thereof, or in which an analog of exendin-4 is selected from the group containing desPro$^{36}$ [Asp$^{28}$]exendin-4 (1-39), desPro$^{36}$ [IsoAsp$^{28}$]exendin-4 (1-39), desPro$^{36}$ [Met(O)$^{14}$, Asp$^{28}$]exendin-4 (1-39), desPro$^{36}$ [Met(O)$^{14}$, IsoAsp$^{28}$]exendin-4 (1-39), desPro$^{36}$ [Trp(O$_2$)$^{25}$, Asp$^{28}$]exendin-2 (1-39), desPro$^{36}$ [Trp(O$_2$)$^{25}$, IsoAsp$^{28}$]exendin-2 (1-39), desPro$^{36}$ [Met(O)$^{14}$Trp(O$_2$)$^{25}$, Asp$^{28}$]exendin-4 (1-39) and

desPro$^{36}$ [Met(O)$^{14}$Trp(O$_2$)$^{25}$, IsoAsp$^{28}$]exendin-4 (1-39), or a pharmacologically tolerable salt thereof.

The invention further provides a pharmaceutical formulation as described above in which the peptide Lys$_6$-NH$_2$ is attached to the C-termini of the analogs of exendin-4.

The invention further provides a pharmaceutical formulation as described above, in which an analog of exendin-4 is selected from the group containing H-(Lys)$_6$-des Pro$^{36}$ [Asp$^{28}$]exendin-4(1-39)-Lys$_6$-NH$_2$ des Asp$^{28}$Pro$^{36}$, Pro$^{37}$, Pro$^{38}$ exendin-4(1-39)-NH$_2$, H-(Lys)$_6$-des Pro$^{36}$, Pro$^{37}$, Pro$^{38}$ [Asp$^{28}$]exendin-4(1-39)-NH$_2$, H-Asn-(Glu)$_5$ des Pro$^{36}$, Pro$^{37}$, Pro$^{38}$ [Asp$^{28}$]exendin-4(1-39)-NH$_2$, des Pro$^{36}$, Pro$^{37}$, Pro$^{38}$ [Asp$^{28}$]exendin-4(1-39)-(Lys)$_6$-NH$_2$, H-(Lys)$_6$-des Pro$^{36}$, Pro$^{37}$, Pro$^{38}$ [Asp$^{28}$]exendin-4(1-39)-(Lys)$_6$-NH$_2$, H-Asn-(Glu)$_5$-des Pro$^{36}$, Pro$^{37}$, Pro$^{38}$ [Asp$^{28}$]exendin-4(1-39)-(Lys)$_6$-NH$_2$, H-(Lys)$_6$-des Pro$^{36}$ [Trp(O$_2$)$^{25}$, Asp$^{28}$]exendin-4(1-39)-Lys$_6$-NH$_2$, H-des Asp$^{28}$ Pro$^{36}$, Pro$^{37}$, Pro$^{38}$ [Trp(O$_2$)$^{25}$]exendin-4(1-39)-NH$_2$, H-(Lys)$_6$-des Pro$^{36}$, Pro$^{37}$, Pro$^{38}$ [Trp(O$_2$)$^{25}$, Asp$^{28}$]exendin-4(1-39)-NH$_2$, H-Asn-(Glu)$_5$-des Pro$^{36}$, Pro$^{37}$, Pro$^{38}$ [Trp(O$_2$)$^{25}$, Asp$^{28}$] exendin-4(1-39)-NH$_2$, des Pro$^{36}$, Pro$^{37}$, Pro$^{38}$ [Trp(O$_2$)$^{25}$, Asp$^{28}$]exendin-4(1-39)-(Lys)$_6$-NH$_2$, H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$, H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)$_6$-NH$_2$, H-(Lys)$_6$-des Pro$^{36}$ [Met(O)$^{14}$, Asp$^{28}$]exendin-4(1-39)-Lys$_6$-NH$_2$, des Met(O)$^{14}$ Asp$^{28}$ Pro$^{36}$, Pro$^{37}$, Pro$^{38}$ exendin-4(1-39)-NH$_2$, H-(Lys)$_6$-des Pro$^{36}$, Pro$^{37}$, Pro$^{38}$ [Met(O)$^{14}$, Asp$^{28}$]exendin-4(1-39)-NH$_2$, H-Asn-(Glu)$_5$-des Pro$^{36}$, Pro$^{37}$, Pro$^{38}$ [Met(O)$^{14}$, Asp$^{28}$] exendin-4(1-39)-NH$_2$, des Pro$^{36}$, Pro$^{37}$, Pro$^{38}$ [Met(O)$^{14}$, Asp$^{28}$]exendin-4(1-39)-(Lys)$_6$-NH$_2$, H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$, H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$, H-(Lys)$_6$-des Pro$^{36}$ [Met(O)$^{14}$, Trp(O$_2$)$^{25}$, Asp$^{28}$]exendin-4(1-39)-Lys$_6$-NH$_2$, des Asp$^{28}$ Pro$^{36}$, Pro$^{37}$, Pro$^{38}$ [Met(O)$^{14}$, Trp(O$_2$)$^{25}$]exendin-4(1-39)-NH$_2$, H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$, H-Asn-(Glu)$_5$-des Pro$^{36}$, Pro$^{37}$, Pro$^{38}$ [Met(O)$^{14}$, Asp$^{28}$] exendin-4(1-39)-NH$_2$, des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$, H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$, H-Asn-(Glu)$_6$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$, or a pharmacologically tolerable salt thereof.

The invention further provides a pharmaceutical formulation as described above, further comprising Arg$^{34}$, Lys$^{26}$

(N$^\varepsilon$($\gamma$-glutamyl(N$^\alpha$-hexadecanoyl))) GLP-1 (7-37) [liraglutide] or a pharmacologically tolerable salt thereof.

The invention further provides a pharmaceutical formulation as described above, comprising methionine in a concentration range of up to 10 mg/ml, preferably up to 3 mg/ml.

The invention further provides a process for preparing a formulation as described above, which comprises (a) introducing the components into an aqueous solution and (b) adjusting the pH.

The invention further provides for the use of a formulation as described above for treating diabetes mellitus.

The invention provides a medicament for treating diabetes mellitus, composed of a formulation as described above.

The specification is described below with reference to a number of examples, which are not intended to have any restrictive effect whatsoever.

KEY TO FIGURES

Figure 2:
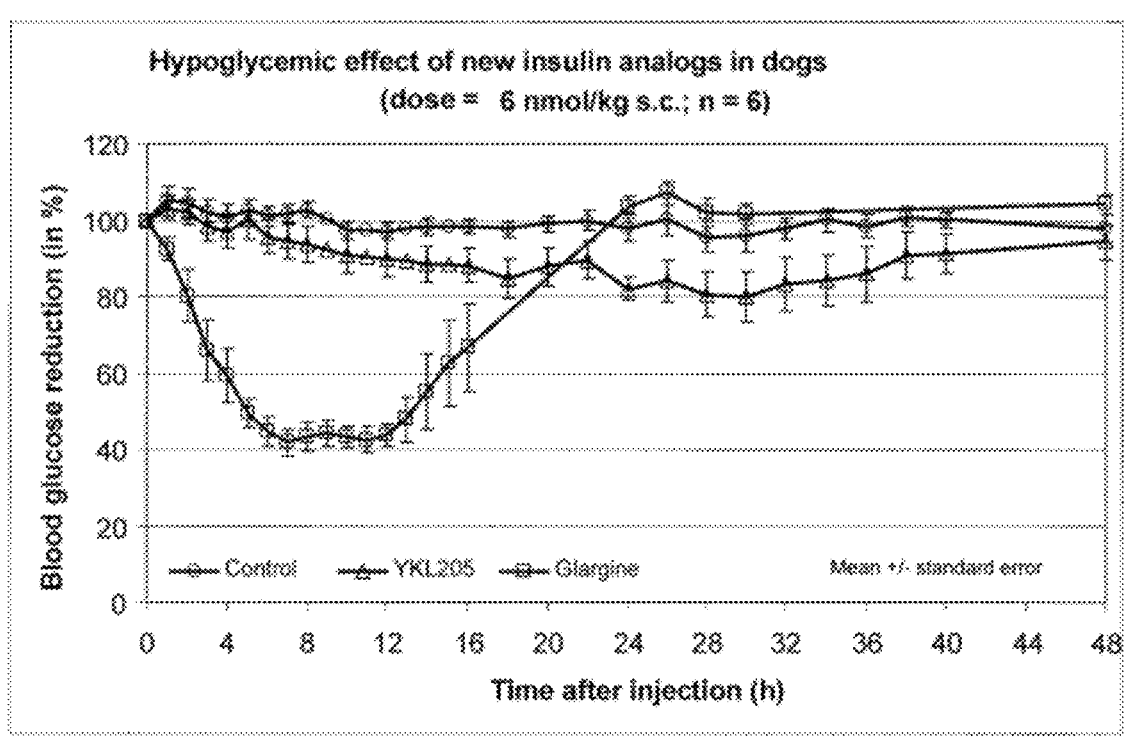
Figure 3:
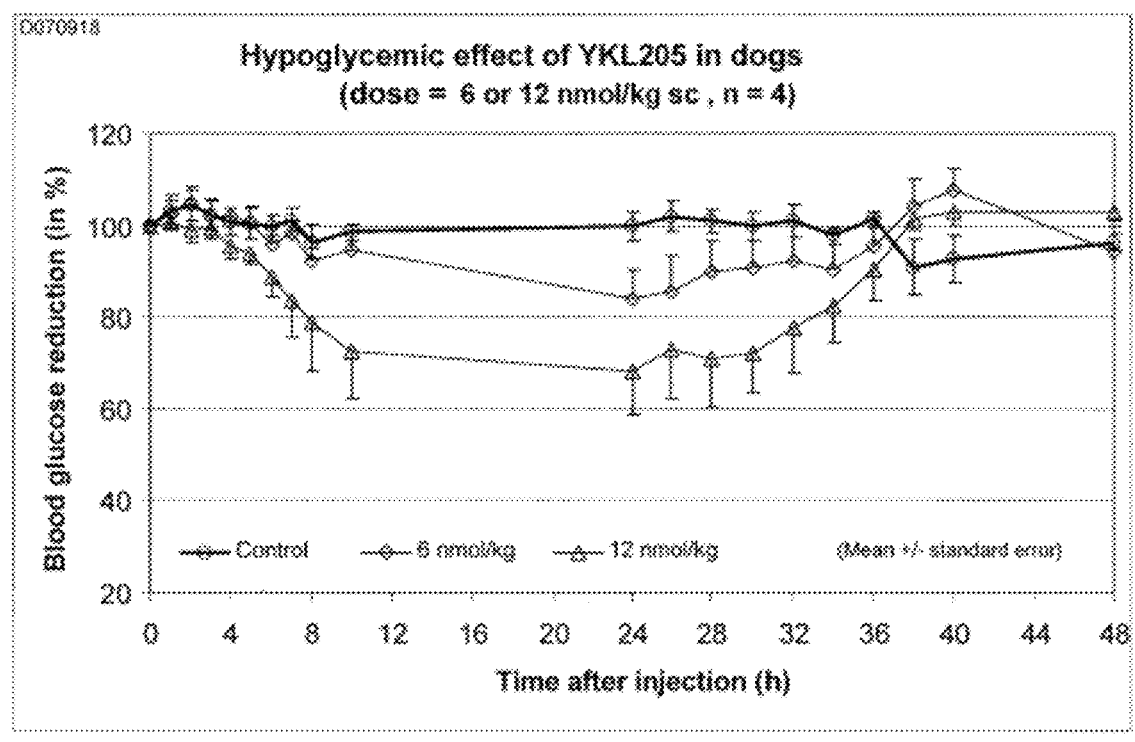
Figure 4:
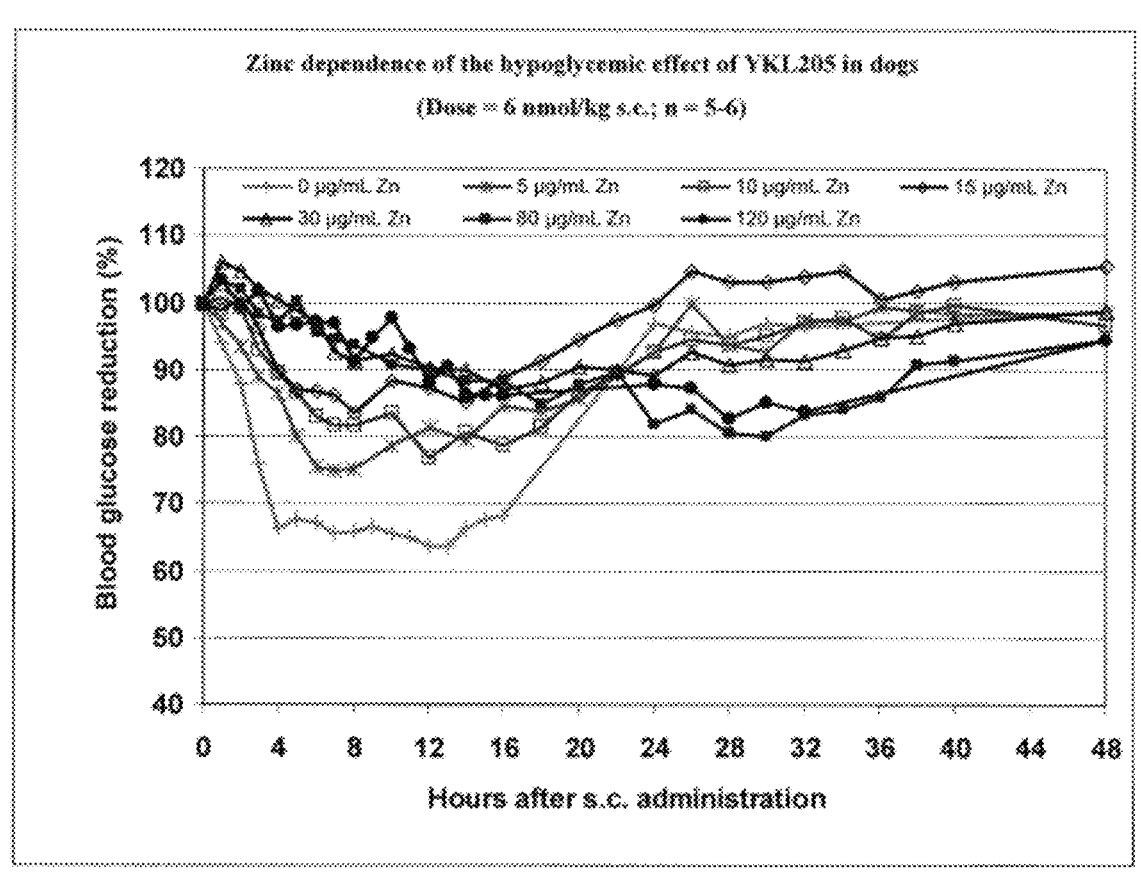
Figure 5:
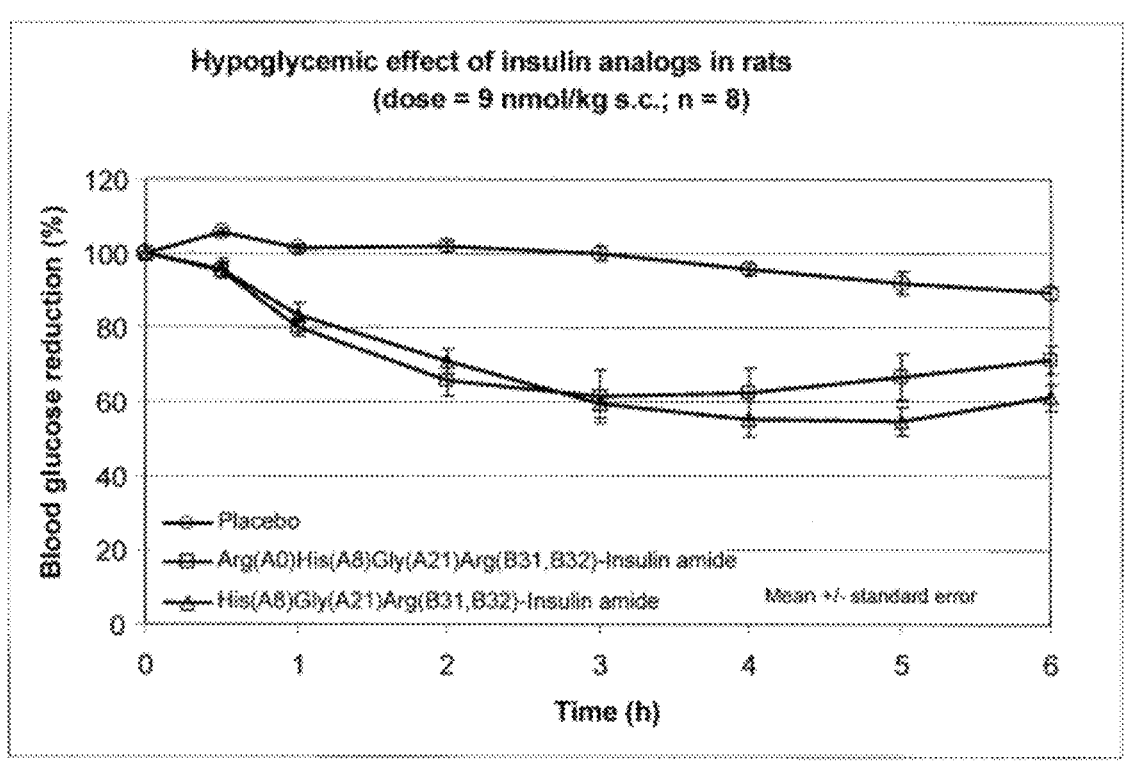
Figure 6:
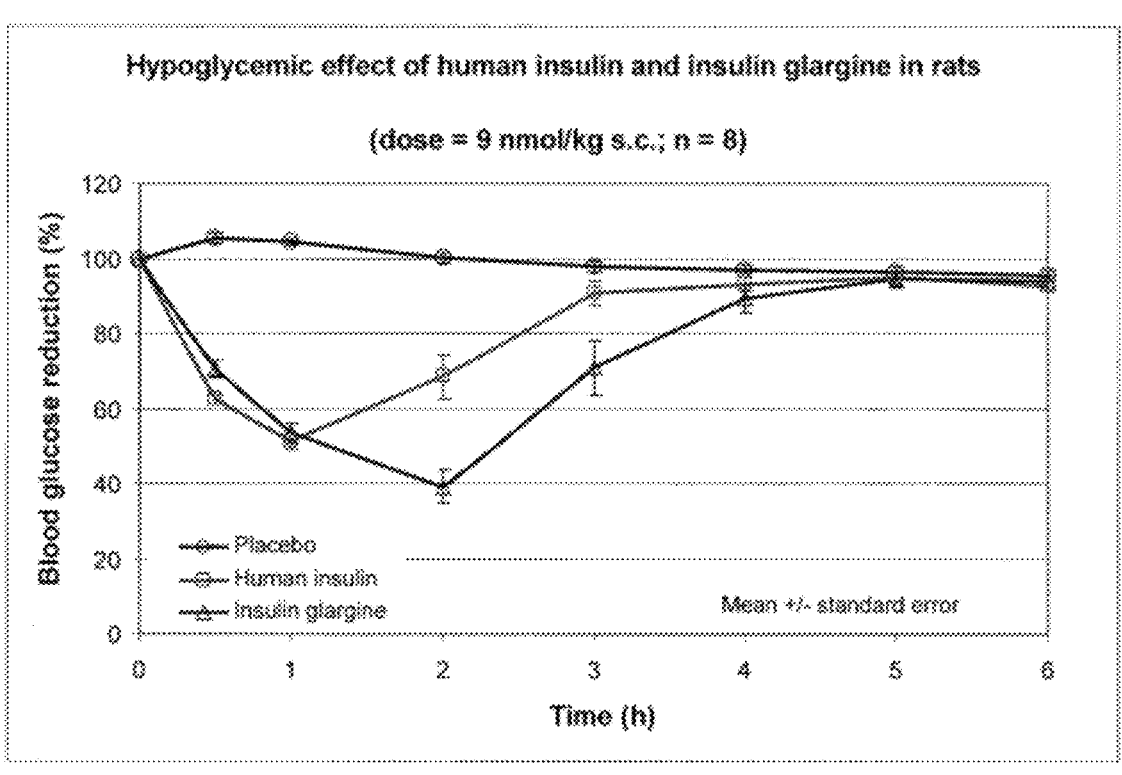

FIG. 1: blood sugar reducing effect of new insulin analogs of formula I in rats FIG. 2: blood sugar reducing effect of new insulin analogs of formula I in dogs FIG. 3: blood sugar reducing effect of YKL205 in dogs FIG. 4: zinc dependence of hypoglycemic effect of YKL205 in dogs FIG. 5: blood sugar reducing effect of inventive insulin analogs of formula II in rats FIG. 6: blood sugar reducing effect of insulin glargine in rats

EXAMPLES

The examples below are intended to illustrate the concept of the invention, without having any restricting effect.

Example 1

Studies on the Dispensing of the Solution Using Nitrogen, Oxygen, and Dispensing Under Standard Conditions The solution is prepared by introducing about 25% of 0.1 M HCl and adding 0.2% of Polysorbate 20 stock solution. In succession, SAR161271 and the zinc chloride stock solution are added and stirred. Adding 1 M HCl at a pH of pH 2 dissolves SAR161271. The solution is stirred and then 1 M NaOH is added to adjust the pH to pH 4.0. Injection-grade water is used to make up to 90% of the batch size. Added to this solution in succession with stirring are glycerol 85% and m-cresol. Injection-grade water is used to make up to the desired final weight. The solution is filtered using a filter attachment on a syringe. The batch was divided into three: ungassed (as reference), gassed with nitrogen and gassed with oxygen (as a positive control). Gassing took place by blanketing with the gas in question.

Untreated

Amount of SAR161271

1 M+5° C.: 3.67 mg/ml

1 M+25° C.: 3.46 mg/ml

1 M+37° C.: 3.41 mg/ml

Impurities

1 M+5° C.: 3.0%

1 M+25° C.: 3.6%

1 M+37° C.: 5.6%

High molecular mass proteins
    1 M+5° C.: 0.2%
    1 M+25° C.: 0.3%
    1 M+37° C.: 1.4%
Nitrogen Treated
    Amount of SAR161271
        1 M+5° C.: 3.73 mg/ml
        1 M+25° C.; 3.50 mg/ml
        1 M+37° C.: 3.35 mg/ml
    Impurities
        1 M+5° C.: 3.1%
        1 M+25° C.: 3.5%
        1 M+37° C.: 5.2%
    High molecular mass proteins
        1 M+5° C.: 0.2%
        1 M+25° C.: 0.3%
        1 M+37° C.:1.2%
Oxygen Treated
    Amount of SAR161271
        1 M+5° C.: 3.54 mg/ml
        1 M+25° C.: 3.34 mg/ml
        1 M+37° C.: 3.26 mg/ml
    Impurities
        1 M+5° C.: 3.2%
        1 M+25° C.: 3.9%
        1 M+37° C.: 7.2%
    High molecular mass proteins
        1 M+5° C.: 0.2%
        1 M+25° C.: 0.5%
        1 M+37° C.:2.9%

In the case of dispensing using nitrogen, there was no distinct reduction in impurities after 1 month as compared with the untreated sample. In the case of dispensing using oxygen, slightly higher impurities and high molecular mass proteins were apparent. On the basis of these results, dispensing under standard conditions was selected.

Example 2

Study of Stability with 3 Different Antioxidants

The solution was prepared as described in example 1. In addition, between the addition of glycerol 85% and m-cresol, the antioxidants—methionine or glutathione or ascorbic acid—were added to the formulation in order to reduce the level of oxidative by-product. The formulations containing either glutathione (0.183 mg/ml) or ascorbic acid (0.105 mg/ml) showed a distinct discoloration after just 3 months of storage. The formulation containing methionine (0.089 mg/ml) showed no discoloration at all and was stable after 1 month of storage at 5° C.
    Amount of SAR161271
        1 M+5° C.: 3.43 mg/ml
        1 M+25° C.: 3.43 mg/ml
        1 M+37° C.: 3.53 mg/ml
    Impurities
        1 M+5° C.: 2.9%
        1 M+25° C.: 3.4%
        1 M+37° C.: 5.7%
High molecular mass proteins
    1 M+5° C.: 0.2%
    1 M+25° C.: 0.3%
    1 M+37° C.: 1.1%

Example 3

Formulation of Amidated Insulin Derivatives

Examples 3 to 7 serve only for the determination of the biological, pharmacological, and physicochemical properties of insulin analogs of formula I, involving first the provision of formulations thereof (example 3) and then the conduct of corresponding tests (examples 4 to 7). A solution with the compounds was prepared as follows: the insulin analog of the invention was dissolved with a target concentration of 240±5 µM in 1 mM hydrochloric acid with 80 µg/ml zinc (as zinc chloride).

The compositions used as dissolution medium were as follows:
    a) 1 mM hydrochloric acid
    b) 1 mM hydrochloric acid, 5 µg/ml zinc (added as zinc chloride or hydrochloric acid)
    c) 1 mM hydrochloric acid, 10 µg/ml zinc (added as zinc chloride or hydrochloric acid)
    d) 1 mM hydrochloric acid, 15 µg/ml zinc (added as zinc chloride or hydrochloric acid)
    e) 1 mM hydrochloric acid, 30 µg/ml zinc (added as zinc chloride or hydrochloric acid)
    f) 1 mM hydrochloric acid, 80 µg/ml zinc (added as zinc chloride or hydrochloric acid)
    g) 1 mM hydrochloric acid, 120 µg/ml zinc (added as zinc chloride or hydrochloric acid)

For this purpose, an amount of the freeze-dried material higher by around 30% than the amount needed on the basis of the molecular weight and the target concentration was first weighed out. Thereafter the existing concentration was determined by means of analytical HPLC and the solution was then made up with 5 mM hydrochloric acid with 80 µg/ml zinc to the volume needed in order to achieve the target concentration. If necessary, the pH was readjusted to 3.5±0.1. Following final analysis by HPLC to ensure the target concentration of 240±5 µM, the completed solution was transferred, using a syringe having a 0.2 µm filter attachment, into a sterile vial which was closed with a septum and a crimped cap. For the short-term, single testing of the insulin derivatives of the invention, there was no optimization of the formulations, in relation, for example, to addition of isotonic agents, preservatives or buffer substances.

Example 4

Evaluation of the Blood Sugar-Reducing Action of New Insulin Analogs in Rats The blood sugar-lowering effect of selected new insulin analogs is tested in healthy male normoglycemic Wistar rats. Male rats receive a subcutaneous injection of a dose of 9 nmol/kg of an insulin analog. Immediately before the injection of the insulin analog and at regular intervals for up to eight hours after injection, blood samples are taken from the animals, and their blood sugar content determined. The experiment shows clearly (cf. FIG. 1) that the insulin analog of the invention leads to a significantly retarded onset of action and to a longer, uniform duration of action.

Example 5

Evaluation of the Blood Sugar-Reducing Action of New Insulin Analogs in Dogs The blood sugar-lowering effect of selected new insulin analogs is tested in healthy male normoglycemic beagles. Male animals receive a subcutaneous injection of a dose of 6 nmol/kg of an insulin analog. Immediately before the injection of the insulin analog and at regular intervals for up to forty-eight hours after injection, blood samples are taken from the animals, and their blood sugar content determined. The experiment shows clearly (cf. FIG. 2) that the insulin analog of the invention that is used leads to a significantly retarded onset of action and to a longer, uniform duration of action.

Example 6

Evaluation of the Blood Sugar-Reducing Action in Dogs with Twofold-Increased Dose The blood sugar-lowering effect of selected new insulin analogs is tested in healthy male normoglycemic beagles. Male animals receive a subcutaneous injection of a dose of 6 nmol/kg and 12 nmol/kg of an insulin analog. Immediately before the injection of the insulin analog and at regular intervals for up to forty-eight hours after injection, blood samples are taken from the animals, and their blood sugar content determined. The experiment shows clearly (cf. FIG. 3) that the insulin analog of the invention that is used has a dose-dependent effect, but that, despite the twofold-increased dose, the effect profile is flat, i.e., there is no pronounced low point (nadir) observed. From this it may be inferred that the insulins of the invention, in comparison to known retarded insulins, lead to significantly fewer hypo-glycemic events.

Example 7

Evaluation of the Blood Sugar-Reducing Effect in Dogs with Different Concentrations of Zinc in the Formulation The experiments were carried out as described in example 35. FIG. 4 shows the result. Accordingly, the time/activity curve of the insulin analog of the invention can be influenced through the amount of zinc ions in the formulation, with the same concentration of insulin, in such a way that a rapid onset of action is observed at zero or low zinc content and the action persists over 24 hours, whereas, with a higher zinc content, a flat onset of action is observed and the insulin effect persists for much longer than 24 hours.

Example 8

Formulation of Amidated Insulin Derivatives

Examples 8 to 10 serve only for the determination of the biological, pharmacological, and physicochemical properties of insulin analogs of formula II, involving first the provision of formulations thereof (example 8) and then the conduct of corresponding tests (examples 9 and 10). The insulin analog of the invention was dissolved with a target concentration of 240±5 µM in 1 mM hydrochloric acid with 80 µg/ml zinc (as zinc chloride). For this purpose, an amount of the freeze-dried material higher by around 30% than the amount needed on the basis of the molecular weight and the target concentration was first weighed out. Thereafter the existing concentration was determined by means of analytical HPLC and the solution was then made up with 5 mM hydrochloric acid with 80 µg/ml zinc to the volume needed in order to achieve the target concentration. If necessary, the pH was readjusted to 3.5±0.1. Following final analysis by HPLC to ensure the target concentration of 240±5 µM, the completed solution was transferred, using a syringe having a 0.2 µm filter attachment, into a sterile vial which was closed with a septum and a crimped cap. For the short-term, single testing of the insulin derivatives of the invention, there was no optimization of the formulations, in relation, for example, to addition of isotonic agents, preservatives or buffer substances.

Example 9

Evaluation of the Blood Sugar-Reducing Action of New Insulin Analogs in Rats The blood sugar-lowering effect of selected new insulin analogs is tested in healthy male normoglycemic Wistar rats. Male rats receive a subcutaneous injection of a dose of 9 nmol/kg of an insulin analog. Immediately before the injection of the insulin analog and at regular intervals for up to eight hours after injection, blood samples are taken from the animals, and their blood sugar content determined. The experiment shows clearly (cf. FIG. 5) that the insulin analog of the invention leads to a significantly retarded onset of action and to a longer, uniform duration of action.

Example 10

Evaluation of the Blood Sugar-Reducing Action of New Insulin Analogs in Dogs The blood sugar-lowering effect of selected new insulin analogs is tested in healthy male normoglycemic beagles. Male animals receive a subcutaneous injection of a dose of 6 nmol/kg of an insulin analog. Immediately before the injection of the insulin analog and at regular intervals for up to forty-eight hours after injection, blood samples are taken from the animals, and their blood sugar content determined. The experiment shows clearly that the insulin analog of the invention leads to a significantly retarded, flat onset of action and to a longer, uniform duration of action.

What is claimed is:

1. An aqueous liquid pharmaceutical formulation comprising about 240 to 3000 nmol/ml Gly(A21), Arg(B31), Arg(B32) human insulin, about 0.089 to about 3.0 mg/ml of methionine as an antioxidative stabilizer, about 0.01 to about 0.08 mg/mL of zinc, about 1.0 to about 3.0 mg/ml of m-cresol, and about 20 mg to 30 mg/ml of glycerol, wherein the liquid pharmaceutical formulation has a pH of 2.5 to 4.5, wherein the formulation is a storable solution.

2. The aqueous liquid pharmaceutical formulation of claim 1, wherein the glycerol concentration is 25 mg/ml.

3. The aqueous liquid pharmaceutical formulation of claim 1, wherein the m-cresol concentration is 2 mg/ml.

4. The aqueous liquid pharmaceutical formulation of claim 1, wherein the concentration of the Gly(A21), Arg (B31), Arg(B32) human insulin is about 100 U/ml.

5. The aqueous liquid pharmaceutical formulation of claim 1; wherein the storable solution is administered via injection.

* * * * *

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial
<220> FEATURE:
<223> OTHER INFORMATION: A-chain
<220> FEATURE:
<221> NAME/KEY: MISC_FEATURE
<222> LOCATION: (1)..(1)
<223> OTHER INFORMATION: Xaa is Lys or Arg
```

-continued

```
<220> FEATURE:
<221> NAME/KEY: MISC_FEATURE
<222> LOCATION: (6)..(6)
<223> OTHER INFORMATION: Xaa is Asp, Gln or Glu
<220> FEATURE:
<221> NAME/KEY: MISC_FEATURE
<222> LOCATION: (16)..(16)
<223> OTHER INFORMATION: Xaa is Asp, Glu or Gln
<220> FEATURE:
<221> NAME/KEY: MISC_FEATURE
<222> LOCATION: (19)..(19)
<223> OTHER INFORMATION: Xaa is Asp, Glu or Asn

<400> SEQUENCE: 1

Xaa Gly Ile Val Glu Xaa Cys Cys His Ser Ile Cys Ser Leu Tyr Xaa
1               5                   10                  15

Leu Glu Xaa Tyr Cys Gly
            20

<210> SEQ ID NO 2
<211> LENGTH: 34
<212> TYPE: PRT
<213> ORGANISM: Artificial
<220> FEATURE:
<223> OTHER INFORMATION: B-chain
<220> FEATURE:
<221> NAME/KEY: MISC_FEATURE
<222> LOCATION: (1)..(1)
<223> OTHER INFORMATION: Xaa is Asp, Glu or absent
<220> FEATURE:
<221> NAME/KEY: MISC_FEATURE
<222> LOCATION: (2)..(2)
<223> OTHER INFORMATION: Xaa is Asp, Glu or absent
<220> FEATURE:
<221> NAME/KEY: MISC_FEATURE
<222> LOCATION: (3)..(3)
<223> OTHER INFORMATION: Xaa is Asp, Glu or Phe
<220> FEATURE:
<221> NAME/KEY: MISC_FEATURE
<222> LOCATION: (4)..(4)
<223> OTHER INFORMATION: Xaa is Asp, Glu or Val
<220> FEATURE:
<221> NAME/KEY: MISC_FEATURE
<222> LOCATION: (5)..(5)
<223> OTHER INFORMATION: Xaa is Asp, Glu or Asn
<220> FEATURE:
<221> NAME/KEY: MISC_FEATURE
<222> LOCATION: (6)..(6)
<223> OTHER INFORMATION: Xaa is Asp, Glu or Gln
<220> FEATURE:
<221> NAME/KEY: MISC_FEATURE
<222> LOCATION: (31)..(31)
<223> OTHER INFORMATION: Xaa is Lys or absent
<220> FEATURE:
<221> NAME/KEY: MISC_FEATURE
<222> LOCATION: (32)..(32)
<223> OTHER INFORMATION: Xaa is Thr or absent
<220> FEATURE:
<221> NAME/KEY: MISC_FEATURE
<222> LOCATION: (33)..(33)
<223> OTHER INFORMATION: Xaa is Arg, Lys or absent
<220> FEATURE:
<221> NAME/KEY: MISC_FEATURE
<222> LOCATION: (34)..(34)
<223> OTHER INFORMATION: Xaa is Arg-Amid, Lys-Amid or absent

<400> SEQUENCE: 2

Xaa Xaa Xaa Xaa Xaa Xaa His Leu Cys Gly Ser His Leu Val Glu Ala
1               5                   10                  15

Leu Tyr Leu Val Cys Gly Glu Arg Gly Phe Phe Tyr Thr Pro Xaa Xaa
            20                  25                  30

Xaa Xaa
```

-continued

```
<210> SEQ ID NO 3
<211> LENGTH: 23
<212> TYPE: PRT
<213> ORGANISM: Artificial
<220> FEATURE:
<223> OTHER INFORMATION: A-chain
<220> FEATURE:
<221> NAME/KEY: MISC_FEATURE
<222> LOCATION: (1)..(1)
<223> OTHER INFORMATION: Xaa is Lys, Arg or absent
<220> FEATURE:
<221> NAME/KEY: MISC_FEATURE
<222> LOCATION: (2)..(2)
<223> OTHER INFORMATION: Xaa is Lys, Arg or absent
<220> FEATURE:
<221> NAME/KEY: MISC_FEATURE
<222> LOCATION: (3)..(3)
<223> OTHER INFORMATION: Xaa is Arg or Gly
<220> FEATURE:
<221> NAME/KEY: MISC_FEATURE
<222> LOCATION: (7)..(7)
<223> OTHER INFORMATION: Xaa is Asp, Glu or Gln
<220> FEATURE:
<221> NAME/KEY: MISC_FEATURE
<222> LOCATION: (17)..(17)
<223> OTHER INFORMATION: Xaa is Asp, Glu or Gln
<220> FEATURE:
<221> NAME/KEY: MISC_FEATURE
<222> LOCATION: (20)..(20)
<223> OTHER INFORMATION: Xaa is Asp, Glu or Asn
<220> FEATURE:
<221> NAME/KEY: MISC_FEATURE
<222> LOCATION: (23)..(23)
<223> OTHER INFORMATION: Xaa is Ala, Ser, Thr or Gly

<400> SEQUENCE: 3

Xaa Xaa Xaa Ile Val Glu Xaa Cys Cys His Ser Ile Cys Ser Leu Tyr
1               5                   10                  15

Xaa Leu Glu Xaa Tyr Cys Xaa
            20

<210> SEQ ID NO 4
<211> LENGTH: 34
<212> TYPE: PRT
<213> ORGANISM: Artificial
<220> FEATURE:
<223> OTHER INFORMATION: B-chain
<220> FEATURE:
<221> NAME/KEY: MISC_FEATURE
<222> LOCATION: (1)..(1)
<223> OTHER INFORMATION: Xaa is Asp, Glu or absent
<220> FEATURE:
<221> NAME/KEY: MISC_FEATURE
<222> LOCATION: (2)..(2)
<223> OTHER INFORMATION: Xaa is Asp, Glu or absent
<220> FEATURE:
<221> NAME/KEY: MISC_FEATURE
<222> LOCATION: (3)..(3)
<223> OTHER INFORMATION: Xaa is Asp, Glu, Phe or absent
<220> FEATURE:
<221> NAME/KEY: MISC_FEATURE
<222> LOCATION: (5)..(5)
<223> OTHER INFORMATION: Xaa is Asp, Glu or Asn
<220> FEATURE:
<221> NAME/KEY: MISC_FEATURE
<222> LOCATION: (6)..(6)
<223> OTHER INFORMATION: Xaa is Asp, Glu or Gln
<220> FEATURE:
<221> NAME/KEY: MISC_FEATURE
<222> LOCATION: (31)..(31)
<223> OTHER INFORMATION: Xaa is Arg, Lys or an amino acid chosen from a
      group containing the amino acids Phe, Ala, Thr, Ser, Val, Leu, Glu
      or Asp, or a chemical bond
<220> FEATURE:
<221> NAME/KEY: MISC_FEATURE
```

-continued

```
<222> LOCATION: (32)..(32)
<223> OTHER INFORMATION: Xaa is Thr or absent
<220> FEATURE:
<221> NAME/KEY: MISC_FEATURE
<222> LOCATION: (33)..(33)
<223> OTHER INFORMATION: Xaa is Arg, Lys or absent
<220> FEATURE:
<221> NAME/KEY: MISC_FEATURE
<222> LOCATION: (34)..(34)
<223> OTHER INFORMATION: Xaa is Arg-Amid or Lys-Amid

<400> SEQUENCE: 4

Xaa Xaa Xaa Val Xaa Xaa His Leu Cys Gly Ser His Leu Val Glu Ala
1               5                   10                  15

Leu Tyr Leu Val Cys Gly Glu Arg Gly Phe Phe Tyr Thr Pro Xaa Xaa
            20                  25                  30

Xaa Xaa
```